US012767552B2

(12) United States Patent
Furudate et al.

(10) Patent No.: US 12,767,552 B2
(45) Date of Patent: Oct. 20, 2026

(54) TITANIUM OXIDE PARTICLE-METAL PARTICLE COMPOSITION AND METHOD FOR PRODUCING SAME

(71) Applicant: Shin-Etsu Chemical Co., Ltd., Tokyo (JP)

(72) Inventors: Manabu Furudate, Kamisu (JP); Tomohiro Inoue, Kamisu (JP); Mikiya Hinoue, Kamisu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 461 days.

(21) Appl. No.: 18/287,766

(22) PCT Filed: Apr. 19, 2022

(86) PCT No.: PCT/JP2022/018154

§ 371 (c)(1),
(2) Date: Oct. 20, 2023

(87) PCT Pub. No.: WO2022/224953

PCT Pub. Date: Oct. 27, 2022

(65) Prior Publication Data

US 2024/0182320 A1 Jun. 6, 2024

(30) Foreign Application Priority Data

Apr. 21, 2021 (JP) ................................ 2021-072099

(51) Int. Cl.

| | |
|---|---|
| ***C01G 23/08*** | (2006.01) |
| ***A61L 2/238*** | (2006.01) |
| ***B01J 35/30*** | (2024.01) |
| ***C01G 23/04*** | (2006.01) |
| ***C01G 23/047*** | (2006.01) |

(52) U.S. Cl.

CPC .............. *C01G 23/08* (2013.01); *A61L 2/238* (2013.01); *B01J 35/30* (2024.01); *C01G 23/04* (2013.01); *C01G 23/047* (2013.01); *B01J 2235/15* (2024.01); *C01P 2002/70* (2013.01); *C01P 2004/51* (2013.01); *C01P 2004/62* (2013.01); *C01P 2004/64* (2013.01)

(58) Field of Classification Search

CPC ...... C01G 23/08; C01G 23/04; C01G 23/047; A61L 2/238; C01P 2002/70; C01P 2004/51; C01P 2004/62; C01P 2004/64; B01J 35/30; B01J 2235/15

See application file for complete search history.

(56) References Cited

U.S. PATENT DOCUMENTS

| | | | | |
|---|---|---|---|---|
| 8,603,302 | B2 | 12/2013 | Hashimoto et al. | |
| 9,604,198 | B2 | 3/2017 | Furudate et al. | |
| 10,737,241 | B2 | 8/2020 | Furudate et al. | |
| 11,446,640 | B2 | 9/2022 | Furudate et al. | |
| 2004/0067193 | A1 * | 4/2004 | Sakatani ............ | C01G 23/0536 423/608 |
| 2011/0198210 | A1 | 8/2011 | Hashimoto et al. | |
| 2012/0214667 | A1 | 8/2012 | Furudate et al. | |
| 2012/0294914 | A1 * | 11/2012 | Tooley ................. | A61K 8/0241 424/59 |
| 2015/0273440 | A1 | 10/2015 | Furudate et al. | |
| 2018/0117567 | A1 | 5/2018 | Furudate et al. | |
| 2019/0099741 | A1 | 4/2019 | Furudate et al. | |

FOREIGN PATENT DOCUMENTS

| | | | |
|---|---|---|---|
| JP | 7-303835 | A | 11/1995 |
| JP | 2000-51708 | A | 2/2000 |
| JP | 2004-283646 | A | 10/2004 |
| JP | 2008-260684 | A | 10/2008 |
| JP | 2009-148700 | A | 7/2009 |
| JP | 2010-104913 | A | 5/2010 |
| JP | 2011-240247 | A | 12/2011 |
| JP | 2012-210632 | A | 11/2012 |
| JP | 2013-198890 | A | 10/2013 |
| JP | 2019-63712 | A | 4/2019 |
| WO | WO 2014/045861 | A1 | 3/2014 |
| WO | WO 2016/152487 | A1 | 9/2016 |

OTHER PUBLICATIONS

International Search Report (PCT/ISA/210) issued in PCT/JP2022/018154 mailed on Jun. 28, 2022.

Written Opinion (PCT/ISA/237) issued in PCT/JP2022/018154 mailed on Jun. 28, 2022.

* cited by examiner

*Primary Examiner* — Wayne A Langel

(74) *Attorney, Agent, or Firm* — Birch, Stewart, Kolasch & Birch, LLP

(57) ABSTRACT

Provided are a titanium oxide particle-metal particle composition having a higher photocatalytic activity, especially a higher visible light activity than before; and a method for producing such composition. The composition contains two kinds of particles which are:

(i) titanium oxide particles with a tin component and a visible light activity-enhancing transition metal component being solid-dissolved therein, and with the surfaces of the titanium oxide particles being modified by an iron component and a silicon component that are not solid-dissolved in the titanium oxide particles; and (ii) antimicrobial metal-containing metal particles.

15 Claims, No Drawings

TITANIUM OXIDE PARTICLE-METAL PARTICLE COMPOSITION AND METHOD FOR PRODUCING SAME

TECHNICAL FIELD

The present invention relates to a titanium oxide particle-metal particle composition and a method for producing the same. Specifically, the invention relates to a titanium oxide particle-metal particle composition (a dispersion liquid, a photocatalyst thin film formed using the dispersion liquid, a member having the photocatalyst thin film on its surface) capable of being easily turned into a highly transparent photocatalyst thin film exhibiting an antimicrobial property regardless of whether or not it is under light irradiation; and a method for producing the same.

BACKGROUND ART

In recent years, consumers have become more demanding for a hygienic living environment, and there is a growing interest in household goods that have been processed to maintain cleanliness, such as those having antimicrobial, antifungal, antiviral, deodorant, and antifouling properties.

Photocatalyst materials have attracted attention as they are widely effective in cleaning base material surfaces by exerting, for example, antimicrobial, antifungal, antiviral, deodorant, and antifouling properties that are brought about by photocatalytic reactions occurring when exposed to lights such as sunlight or artificial lighting.

A photocatalytic reaction is a reaction caused by excited electrons and positive holes that are generated when a photocatalyst as typified by titanium oxide absorbs light. Excited electrons and positive holes generated on the surface of titanium oxide by a photocatalytic reaction undergo a redox reaction with oxygen and water adsorbed on the surface of titanium oxide to generate active species. Microorganisms, viruses, odors, and stains that are composed of organic matters are decomposed by these active species; it is assumed that due to this reason, there can be achieved the effect of cleaning base material surfaces as described above.

It can be said that the strengths of photocatalysts are, for example, the fact that they are effective against a wide variety of microorganisms, viruses, odors, and stains as they can be basically used against any organic matter, and the fact that they hardly deteriorate over time.

Recently, as for the application of the above photocatalytic action, studies are being conducted on uses not only outdoors where ultraviolet light (wavelength 10 to 400 nm) is available, but also indoors where a light source(s) mostly composed of lights in the visible region (wavelength 400 to 800 nm), such as a fluorescent light, are used for illumination. For example, as a visible light responsive photocatalyst, there has been developed a tungsten oxide photocatalyst body (JP-A-2009-148700: Patent document 1).

As a method for enhancing the visible light activity of a photocatalyst utilizing titanium oxide, there are known, for example, a method of having iron and/or copper supported on the surfaces of titanium oxide fine particles and titanium oxide fine particles doped with a metal (e.g. JP-A-2012-210632: Patent document 2, JP-A-2010-104913: Patent document 3. JP-A-2011-240247: Patent document 4, JP-A-Hei-7-303835: Patent document 5); a method where there are at first separately prepared titanium oxide fine particles with tin and a visible light activity-enhancing transition metal solid-dissolved (doped) therein and titanium oxide fine particles with copper solid-dissolved therein, followed by mixing them before use (WO2014/045861: Patent document 6); and a method where there are at first separately prepared titanium oxide fine particles with tin and a visible light responsiveness-enhancing transition metal solid-dissolved therein and titanium oxide fine particles with an iron group element solid-dissolved therein, followed by mixing them before use (WO2016/152487: Patent document 7).

As a result of employing a photocatalyst film formed using a visible light-responsive photocatalyst titanium oxide fine particle dispersion liquid that is obtained by mixing the separately prepared titanium oxide fine particles with tin and a visible light activity-enhancing transition metal solid-dissolved therein and the separately prepared titanium oxide fine particles with an iron group element solid-dissolved therein as is the case with patent document 7, a high decomposition activity can be achieved under a condition where only lights in the visible region are available. Further, it has been demonstrated that an acetaldehyde gas can be likewise decomposed under a condition where only lights in the visible region are available even when employing a photocatalyst thin film formed using a titanium oxide fine particle dispersion liquid in which an iron component is adsorbed to (=supported on) the surfaces of titanium oxide fine particles with tin and a visible light activity-enhancing transition metal being solid-dissolved therein; however, a low photocatalytic activity was observed as a result of restricting the addable amount of the iron component due to the fact that the quality of the photocatalyst film obtained will be impaired as the titanium oxide fine particles agglutinate and precipitate because of the iron component.

As described above, although a number of studies are being conducted to improve photocatalytic activity, further improvements in photocatalytic activity are demanded as it is critical to decompose and eliminate hazardous substances as rapidly as possible in the actual environment.

Further, since a photocatalytic reaction is caused by irradiation with lights in the ultraviolet region (wavelength 10 to 400 nm) or lights in the visible region (wavelength 400 to 800 nm), the effects thereof cannot be technically achieved in dark places that are not exposed to natural lights or artificial lighting.

Meanwhile, since bacteria and fungi (molds) can proliferate even without lights, there is demanded a material capable of exhibiting an antimicrobial property even in dark places that are not exposed to lights in the case of a product requiring a certain property to last for a desired period of time, such as an antimicrobial product.

In order to address the above problem, a photocatalyst material with an enriched photocatalytic function is being considered by combining a photocatalyst with an antimicrobial agent other than a photocatalyst. Since a photocatalyst decomposes organic substances, it is appropriate that an inorganic antimicrobial material be used. For example, it is disclosed that by adding silver, copper or the like as an antimicrobial-antifungal component, there can be achieved an antimicrobial property and antifungal property in dark places (JP-A-2000-051708: Patent document 8, JP-A-2008-260684: Patent document 9).

In general, a photocatalyst is used in a manner such that photocatalyst particles are to be dispersed in a solvent, followed by mixing a film-forming component(s) thereinto to produce a coating material, and then applying such coating material to a base material. However, as described above, practical problems have often occurred as a result of adding metal components such as silver, copper and zinc to improve antimicrobial capability. That is, as a method for supporting metals such as silver, copper and zinc; or even compounds thereof, it is not preferable to support them by reacting a photocatalyst particle powder with a metal raw material(s) because a great effort needs to be made afterward to disperse the reacted ingredients in a solvent. Further, if adding a metal raw material(s) to a dispersion liquid with photocatalyst particles already being dispersed therein, a dispersion stability of the photocatalyst particles will be inhibited, which will cause agglomeration in a way such that it is often difficult to achieve a practically required transparency when forming such a type of photocatalyst thin film on various base materials.

Further, in the case of a photocatalyst of the type in which a photocatalytic activity-improving component is attached to the photocatalyst surface, there is also a problem that simply adding these metal components will weaken the effect of attaching the photocatalytic activity-improving component, whereby a photocatalytic function expected cannot be achieved, which is why there has never been a photocatalyst thin film that has both an antimicrobial property sufficient for practical use and a transparency required for application to various base materials.

PRIOR ART DOCUMENTS

Patent Documents

Patent document 1: JP-A-2009-148700
Patent document 2: JP-A-2012-210632
Patent document 3: JP-A-2010-104913
Patent document 4: JP-A-2011-240247
Patent document 5: JP-A-Hei-7-303835
Patent document 6: WO2014/045861
Patent document 7: WO2016/152487
Patent document 8: JP-A-2000-051708
Patent document 9: JP-A-2008-260684

SUMMARY OF THE INVENTION

Problems to be Solved by the Invention

Thus, it is an object of the present invention to provide a titanium oxide particle-metal particle composition having a higher photocatalytic activity, especially a higher visible light activity than before, and exhibiting a high antimicrobial property regardless of whether or not it is under light irradiation; and a method for producing such composition.

Means to Solve the Problems

In order to achieve the above object, the inventors of the present invention extensively conducted a series of studies on, for example, metal elements to be solid-dissolved in titanium oxide particles and combinations thereof, metal elements to modify titanium oxide particles and combinations thereof, combinations of titanium oxide particles and various materials, and quantitative ratios thereof. As a result, the inventors were able to make the present invention by finding that in the case of a titanium oxide particle-metal particle composition containing two kinds of particles which were titanium oxide particles with their surfaces being modified by an iron component and a silicon component and with particular metals being solid-dissolved therein, and antimicrobial metal-containing metal particles prepared separately, a photocatalytic activity of the composition, especially a visible light activity thereof improved dramatically as compared to before, a high antimicrobial property was exhibited regardless of whether or not it was under light irradiation, and there could be easily produced a highly transparent photocatalyst thin film.

That is, the present invention is to provide the following titanium oxide particle-metal particle composition and a method for producing the same.

[1]

A titanium oxide particle-metal particle composition comprising two kinds of particles which are:

(i) titanium oxide particles with a tin component and a visible light activity-enhancing transition metal component being solid-dissolved therein, and with the surfaces of the titanium oxide particles being modified by an iron component and a silicon component that are not solid-dissolved in the titanium oxide particles; and (ii) antimicrobial metal-containing metal particles.

[2]

The titanium oxide particle-metal particle composition according to [1], wherein a protective agent is adsorbed onto the surfaces of the antimicrobial metal-containing metal particles (ii).

[3]

The titanium oxide particle-metal particle composition according to [1] or [2], wherein an antimicrobial metal contained in the antimicrobial metal-containing metal particles (ii) is at least one kind of metal selected from silver, copper and zinc.

[4]

The titanium oxide particle-metal particle composition according to [3], wherein the antimicrobial metal contained in the antimicrobial metal-containing metal particles (ii) at least contains silver.

[5]

The titanium oxide particle-metal particle composition according to any one of [1] to [4], wherein the tin component is contained and solid-dissolved in the titanium oxide particles (i) by an amount of 1 to 1,000 in terms of a molar ratio to titanium oxide ($TiO_2/Sn$).

[6]

The titanium oxide particle-metal particle composition according to any one of [1] to [5], wherein a mass ratio of the iron component (in terms of oxide) modifying the surfaces of the titanium oxide particles (i) to titanium oxide ($TiO_2/Fe_2O_3$) is 10 to 100,000, and a mass ratio of the silicon component (in terms of oxide) modifying the surfaces of the titanium oxide particles (i) to titanium oxide ($TiO_2/SiO_2$) is 1 to 10,000.

[7]

The titanium oxide particle-metal particle composition according to any one of [1] to [6], wherein the visible light activity-enhancing transition metal component solid-dissolved in the titanium oxide particles (i) is at least one kind selected from molybdenum, tungsten and vanadium.

[8]

The titanium oxide particle-metal particle composition according to [7], wherein the molybdenum, tungsten and vanadium components are each solid-dissolved in the titanium oxide particles (i) by an amount of 1 to 10,000 in terms of a molar ratio to titanium oxide ($TiO_2/Mo$, $TiO_2/W$ or $TiO_2/V$).

[9]

The titanium oxide particle-metal particle composition according to any one of [1] to [8], wherein a mass ratio between the titanium oxide particles (i) and an antimicrobial metal component (M) contained in the metal particles (ii) ($TiO_2/M$) is 1 to 100,000.

[10]

The titanium oxide particle-metal particle composition according to any one of [1] to [9], wherein the composition further comprises a binder.

[11]

The titanium oxide particle-metal particle composition according to [10], wherein the binder is a silicon compound-based binder.

[12]

The titanium oxide particle-metal particle composition according to any one of [1] to [11], wherein the composition is a titanium oxide particle-metal particle dispersion liquid.

[13]

The titanium oxide particle-metal particle composition according to any one of [1] to [11], wherein the composition is a titanium oxide particle-metal particle thin film.

[14]

A member having the composition according to on a surface thereof.

[15]

A method for producing the composition according to [12], comprising:

(1) a step of producing a tin component and transition metal component-containing peroxotitanic acid solution from a raw material titanium compound, tin compound, transition metal compound, basic substance, hydrogen peroxide and aqueous dispersion medium;
(2) a step of obtaining a dispersion liquid of titanium oxide particles with the tin and transition metal components being solid-dissolved therein, by heating the tin component and transition metal component-containing peroxotitanic acid solution produced in the step (1) at 80 to 250° C. under a controlled pressure;
(3) a step of producing a solution or dispersion liquid of an iron component and a silicon component from an iron compound, silicon compound and aqueous dispersion medium;
(4) a step of obtaining a dispersion liquid of titanium oxide particles surface-modified by the iron and silicon components, by mixing the titanium oxide particle dispersion liquid produced in the step (2) and the solution or dispersion liquid of the iron and silicon components that has been produced in the step (3);
(5) a step of respectively producing a solution containing a raw material antimicrobial metal compound, and a solution containing a reductant for reducing the raw material antimicrobial metal compound and a protective agent for coating and protecting metal particles;
(6) a step of producing a metal particle dispersion liquid by mixing the solutions obtained in the step (5) which are the solution containing the raw material antimicrobial metal compound, and the solution containing the reductant for reducing the raw material antimicrobial metal compound and the protective agent for coating and protecting metal particles;
(7) a step of washing the metal particle dispersion liquid produced in the step (6) by a membrane filtration method, using an aqueous dispersion medium; and
(8) a step of mixing the titanium oxide particle dispersion liquid obtained in the step (4) and the metal particle dispersion liquid obtained in the step (7).

Effects of the Invention

The titanium oxide particle-metal particle composition of the present invention has a higher photocatalytic activity than before, especially a high photocatalytic activity even under only a visible light (wavelength 400 to 800 nm), exhibits a high antimicrobial property regardless of whether or not it is under light irradiation, and can be easily tuned into a highly transparent photocatalyst thin film. Thus, the titanium oxide particle-metal particle composition of the present invention is suitable for use in members that require rapid cleaning of their base material surfaces, and are used in indoor spaces illuminated by artificial lightings mostly composed of visible lights such as those delivered from a fluorescent light and a white LED.

MODE FOR CARRYING OUT THE INVENTION

The present invention is described in detail hereunder.

<Titanium Oxide Particle-Metal Particle Composition>

A titanium oxide particle-metal particle composition of the present invention contains two kinds of particles which are:

(i) titanium oxide particles with a tin component and a visible light activity-enhancing transition metal being solid-dissolved therein, and with the surfaces of the titanium oxide particles being modified by an iron component and a silicon component that are not solid-dissolved in the titanium oxide particles; and
(ii) antimicrobial metal-containing metal particles.

One embodiment of the titanium oxide particle-metal particle composition of the present invention is a dispersion liquid of the titanium oxide particles and metal particles of this composition. Further, another embodiment of the titanium oxide particle-metal particle composition of the present invention is a thin film (photocatalyst thin film) of the titanium oxide particles and metal particles of this composition.

At first, described is the embodiment where the titanium oxide particle-metal particle composition of the present invention is the dispersion liquid of the titanium oxide particles and metal particles i.e. titanium oxide particle-metal particle dispersion liquid.

The titanium oxide particle-metal particle dispersion liquid of the present invention is one with the two kinds of particles being dispersed in an aqueous dispersion medium, the two kinds of particles being:

(i) the titanium oxide particles with the tin component and the visible light activity-enhancing transition metal being solid-dissolved therein, and with the surfaces of the titanium oxide particles being modified by the iron component and the silicon component that are not solid-dissolved in the titanium oxide particles; and
(ii) the antimicrobial metal-containing metal particles.

As described later, the titanium oxide particle-metal particle dispersion liquid is obtained by mixing two kinds of separately prepared particle dispersion liquids which are a titanium oxide particle dispersion liquid and a metal particle dispersion liquid.

A content ratio between the titanium oxide particles (i) and an antimicrobial metal component (M) contained in the metal particles (ii) i.e. $TiO_2/M$ is 1 to 100,000, preferably 10 to 10,000, more preferably 100 to 1,000, in terms of mass ratio. It is not preferable if this mass ratio is smaller than 1, because a photocatalytic capability cannot be sufficiently exerted. It is also not preferable if this mass ratio is greater than 100,000, because an antimicrobial capability cannot be sufficiently exerted.

Here, it is preferred that the mixture of the titanium oxide particles and metal particles in the titanium oxide particle-metal particle dispersion liquid have a dispersion particle diameter of 3 to 50 nm, more preferably 3 to 40 nm, even more preferably 3 to 30 nm, the dispersion particle diameter being a 50% cumulative distribution diameter ($D_{50}$) on volumetric basis that is measured by a dynamic light scattering method using a laser light. This is because if $D_{50}$ is smaller than 3 nm, an insufficient photocatalytic activity may be observed; and if $D_{50}$ is greater than 50 nm, the dispersion liquid and the photocatalyst thin film obtained from such dispersion liquid may be opaque.

Further, as for a 90% cumulative distribution diameter ($D_{90}$) thereof on volumetric basis, it is preferred that such diameter be 5 to 100 nm, more preferably 5 to 80 nm, respectively. This is because if $D_{90}$ is smaller than 5 nm, an insufficient photocatalytic activity may be observed; and if $D_{90}$ is greater than 100 nm, the dispersion liquid and the photocatalyst thin film obtained from such dispersion liquid may be opaque.

Here, as a device for measuring the dispersion particle diameter of the mixture of the titanium oxide particles and metal particles, there may be used, for example, ELSZ-2000ZS (by Otsuka Electronics Co., Ltd.), NANOTRAC UPA-EX150 (by Nikkiso Co., Ltd.) or LA-910 (by HORIBA, Ltd.).

Aqueous Dispersion Medium

As the aqueous dispersion medium, while water is preferably used, there may also be used a mixed solvent of water and a hydrophilic organic solvent which is to be mixed with water at any ratio. As water, preferred are, for example, purified waters such as a filtrate water, a deionized water, a distilled water and a pure water. Moreover, as the hydrophilic organic solvent, preferred are, for example, alcohols such as methanol, ethanol and isopropanol; glycols such as ethylene glycol; and glycol ethers such as ethylene glycol monomethyl ether, ethylene glycol monoethyl ether and propylene glycol-n-propyl ether. If using such mixed solvent, it is preferred that a ratio of the hydrophilic organic solvent in the mixed solvent be larger than 0% by mass, but not larger than 50% by mass; more preferably larger than 0% by mass, but not larger than 20% by mass; even more preferably larger than 0% by mass, but not larger than 10% by mass.

(i) Titanium Oxide Particles with Tin Component and Visible Light Activity-Enhancing Transition Metal Component being Solid-Dissolved Therein, and with Surfaces of Titanium Oxide Particles being Modified by Iron Component and Silicon Component that are not Solid-Dissolved in Titanium Oxide Particles The titanium oxide particle component (i) contained in the titanium oxide particle-metal particle dispersion liquid of the present invention is one containing: the titanium oxide particles with the tin component and the visible light activity-enhancing transition metal being solid-dissolved therein; and the iron and silicon components. While the titanium oxide particles are surface-modified by the iron and silicon components, part of the iron and silicon components may remain free in the dispersion liquid.

Here, "modification" refers to allowing various components to adhere to the surface of a solid by reacting these components and allowing them to adsorb thereonto, and is carried out for the purposes of, for example, changing the properties of the surface of the solid, and imparting a novel function thereto.

It is preferred that the titanium oxide particle component (i) be added to the titanium oxide particle-metal particle dispersion liquid of the present invention as a titanium oxide particle dispersion liquid.

The titanium oxide particles are those with the tin component and the visible light activity-enhancing transition metal component being solid-dissolved in titanium oxide used as a photocatalyst, and with the surface of such titanium oxide being modified by the iron and silicon components.

As a crystal phase of titanium oxide particles, there are generally known three of them which are the rutile-type, anatase-type and brookite-type. It is preferred that the titanium oxide particles of the present invention mainly be the anatase-type or rutile-type. Here, the expression "mainly" refers to a condition where the titanium oxide particles having such particular crystal phase(s) are contained in the titanium oxide particles as a whole by an amount of not smaller than 50% by mass, preferably not smaller than 70% by mass, even more preferably not smaller than 90% by mass, or even 100% by mass.

Here, in this specification, a solid solution refers to that having a phase where atoms at lattice points in a certain crystal phase have been substituted by other atoms or where other atoms have entered lattice spacings i.e. a mixed phase regarded as one with a different substance(s) dissolved into a certain crystal phase, and being a homogeneous phase as a crystal phase. A solid solution where solvent atoms at lattice points have been substituted by solute atoms is called a substitutional solid solution, and a solid solution where solute atoms have entered lattice spacings is called an interstitial solid solution; in this specification, a solid solution refers to both of them.

The titanium oxide particles contained in the dispersion liquid are those that have formed a solid solution with tin atoms and transition metal atoms. The solid solution may be either substitutional or interstitial. A substitutional solid solution of titanium oxide is formed by having titanium sites of a titanium oxide crystal substituted by various metal atoms; an interstitial solid solution of titanium oxide is formed by having various metal atoms enter the lattice spacings of a titanium oxide crystal. After various metal atoms have been solid-dissolved into titanium oxide, when measuring the crystal phase by X-ray diffraction or the like, there will only be observed the peak of the crystal phase of titanium oxide, whereas there will not be observed peaks of compounds derived from various metal atoms added.

While there are no particular restrictions on a method for solid-dissolving dissimilar metals into a metal oxide crystal, there may be listed, for example, a gas phase method (e.g. CVD method, PVD method), a liquid phase method (e.g. hydrothermal method, sol-gel process) and a solid phase method (e.g. high-temperature firing).

The tin component to be solid-dissolved in the titanium oxide particles may be that derived from a tin compound, examples of which include elemental tin as a metal (Sp), a tin oxide ($SnO$, $SnO_2$), a tin hydroxide, a tin chloride ($SnCl_2$, $SnCl_4$), a tin nitrate ($Sn(NO_3)_2$), a tin sulfate ($SnSO_4$), a tin halide (Br, I) other than a tin chloride, a salt of tin-oxoacid (stannate) ($Na_2SnO_3$, $K_2SnO_3$) and a tin complex compound; there may be used one of them or a combination of two or more of them. Particularly, it is preferred that there be used a tin oxide ($SnO$, $SnO_2$), a tin chloride ($SnCl_2$, $SnCl_4$), a tin sulfate ($SnSO_4$) and a salt of tin-oxoacid (stannate) ($Na_2SnO_3$, $K_2SnO_3$).

The tin component is solid-dissolved in the titanium oxide particles by an amount of preferably 1 to 1,000, more preferably 5 to 500, even more preferably 5 to 100, in terms of a molar ratio to titanium oxide ($TiO_2/Sn$). This is because if the molar ratio is lower than 1, a photocatalytic effect may not be sufficiently exhibited as titanium oxide is now contained at a lower rate; and if the molar ratio is greater than 1,000, a visible light responsiveness may be insufficient.

The visible light activity-enhancing transition metal to be solid-dissolved in the titanium oxide particles refers to those from the group 3 to group 11 in the periodic table, such as vanadium, chromium, manganese, niobium, molybdenum, rhodium, tungsten, cerium, among which molybdenum, tungsten and vanadium are preferred. In this sense, iron which is a transition metal is not included in visible light activity-enhancing transition metals. Meanwhile, silicon modifies the surfaces of the titanium oxide particles, but is not solid-dissolved in the titanium oxide particles. That is, the titanium oxide particles (i) contained in the titanium oxide particle-metal particle composition of the present invention are those without the iron and silicon components being solid-dissolved therein.

The transition metal component to be solid-dissolved in the titanium oxide particles may be that derived from a corresponding transition metal compound, examples of which include a metal, an oxide, a hydroxide, a chloride, a nitrate, a sulfate, a halide (Br, I) other than a chloride, a salt of oxoacid and various complex compounds; there may be used one of them or a combination of two or more of them.

The amount of the transition metal component(s) to be solid-dissolved in the titanium oxide particles may be appropriately determined based on the type of the transition metal component; it is preferred that the amount thereof be 1 to 10,000 in terms of a molar ratio to titanium oxide ($TiO_2$/transition metal).

The transition metal to be solid-dissolved may be selected from those listed above; particularly, if molybdenum is selected as the transition metal component to be solid-dissolved in the titanium oxide particles, it will suffice if the molybdenum component is that derived from a molybdenum compound, examples of which include elemental molybdenum as a metal (Mo), a molybdenum oxide ($MoO_2$, $MoO_3$), a molybdenum hydroxide, a molybdenum chloride ($MoCl_3$, $MoCl_5$), a molybdenum nitrate, a molybdenum sulfate, a molybdenum halide (Br, I) other than a molybdenum chloride, a molybdic acid (molybdenum-oxoacid) and a salt thereof ($H_2MoO_4$, $Na_2MoO_4$, $K_2MoO_4$), and a molybdenum complex compound; there may be used one of them or a combination of two or more of them. Particularly, it is preferred that there be used a molybdenum oxide ($MoO_2$, $MoO_3$), a molybdenum chloride ($MoCl_3$, $MoCl_5$), and a molybdenum-oxoacid and a salt thereof ($H_2MoO_4$, $Na_2MoO_4$, $K_2MoO_4$).

The molybdenum component is preferably solid-dissolved in the titanium oxide particles by an amount of 1 to 10,000, more preferably 5 to 5,000, even more preferably 20 to 1,000, in terms of a molar ratio to titanium oxide ($TiO_2$/Mo). This is because if the molar ratio is lower than 1, a photocatalytic effect may not be sufficiently exhibited as titanium oxide is now contained at a lower rate; and if the molar ratio is greater than 10,000, an insufficient visible light responsiveness may be observed.

When tungsten is selected as the transition metal component to be solid-dissolved in the titanium oxide particles, it will suffice if the tungsten component is that derived from a tungsten compound, examples of which include elemental tungsten as a metal (W), a tungsten oxide ($WO_3$), a tungsten hydroxide, a tungsten chloride ($WCl_4$, $WCl_6$), a tungsten nitrate, a tungsten sulfate, a tungsten halide (Br, I) other than a tungsten chloride, a tungstic acid and salt of tungsten-oxoacid (tungstate) ($H_2WO_4$, $Na_2WO_4$, $K_2WO_4$), and a tungsten complex compound; there may be used one of them or a combination of two or more of them. Particularly, it is preferred that there be used a tungsten oxide ($WO_3$), a tungsten chloride ($WCl_4$, $WCl_6$) and a salt of tungsten-oxoacid (tungstate) ($Na_2WO_4$, $K_2WO_4$).

The tungsten component is preferably solid-dissolved in the titanium oxide particles by an amount of 1 to 10,000, more preferably 5 to 5,000, even more preferably 20 to 2,000, in terms of a molar ratio to titanium oxide ($TiO_2$/W). This is because if the molar ratio is lower than 1, a photocatalytic effect may not be sufficiently exhibited as titanium oxide is now contained at a lower rate; and if the molar ratio is greater than 10,000, an insufficient visible light responsiveness may be observed.

When vanadium is selected as the transition metal component to be solid-dissolved in the titanium oxide particles, it will suffice if the vanadium component is that derived from a vanadium compound, examples of which include elemental vanadium as a metal (V), a vanadium oxide (VO, $V_2O_3$, $VO_2$, $V_2O_5$), a vanadium hydroxide, a vanadium chloride ($VCl_5$), a vanadium oxychloride ($VOCl_3$), a vanadium nitrate, a vanadium sulfate, a vanadyl sulfate ($VOSO_4$), a vanadium halide (Br, I) other than a vanadium chloride, a salt of vanadium-oxoacid (vanadate) ($Na_3VO_4$, $K_3VO_4$, $KVO_3$), and a vanadium complex compound; there may be used one of them or a combination of two or more of them. Particularly, it is preferred that there be used a vanadium oxide ($V_2O_3$, $V_2O_5$), a vanadium chloride ($VCl_5$), a vanadium oxychloride ($VOCl_3$), a vanadyl sulfate ($VOSO_4$), and a salt of vanadium-oxoacid (vanadate) ($Na_3VO_4$, $K_3VO_4$, $KVO_3$).

The vanadium component is preferably solid-dissolved in the titanium oxide particles by an amount of 1 to 10,000, more preferably 10 to 10,000, even more preferably 100 to 10,000, in terms of a molar ratio to titanium oxide ($TiO_2$/V). This is because if the molar ratio is lower than 1, a photocatalytic effect may not be sufficiently exhibited as titanium oxide is now contained at a lower rate; and if the molar ratio is greater than 10,000, an insufficient visible light responsiveness may be observed.

As the transition metal component(s) to be solid-dissolved in the titanium oxide particles, there may also be selected multiple components from molybdenum, tungsten and vanadium. The amount of each component at that time may be selected from the above ranges. However, a molar ratio between a sum of the components and titanium oxide [$TiO_2$/(Mo+W+V)] is not lower than 1, but lower than 10,000.

As the titanium oxide particles, one kind thereof may be used, or two or more kinds thereof may be used in combination. There may be achieved an effect of enhancing a visible light activity if combining two or more kinds of the titanium oxide particles having different visible light responsivenesses.

The iron and silicon components by which the titanium oxide particles are surface-modified are for enhancing the visible light responsiveness of the photocatalyst thin film.

While the iron component is for enhancing the visible light responsiveness of the photocatalyst thin film, it will suffice if the iron component is that derived from an iron compound, examples of which include elemental iron as a metal (Fe), an iron oxide ($Fe_2O_3$, $Fe_3O_4$), an iron hydroxide ($Fe(OH)_2$, $Fe(OH)_3$), an iron oxyhydroxide (FeO(OH)), an iron chloride ($FeCl_2$, $FeCl_3$), an iron nitrate ($Fe(NO)_3$), an iron sulfate ($FeSO_4$, $Fe_2(SO_4)_3$), an iron halide (Br, I) other than an iron chloride, and an iron complex compound; there may be used one of them or a combination of two or more of them.

The iron component (in terms of oxide) is preferably contained in an amount of 10 to 100,000, more preferably 20 to 10,000, even more preferably 50 to 1,000, in terms of a mass ratio to titanium oxide ($TiO_2/Fe_2O_3$). This is because if the mass ratio is lower than 10, the titanium oxide will agglutinate and precipitate so that the quality of the photocatalyst thin film obtained will deteriorate, and the photocatalytic effect thereof may thus not be exerted in a sufficient manner; and if the mass ratio is greater than 100,000, an insufficient visible light responsiveness may be observed.

The silicon component is for inhibiting deterioration in photocatalytic effect by avoiding deterioration in quality of the photocatalyst thin film as a result of inhibiting the agglutination and precipitation of titanium oxide and the iron component at the time of adding the iron component. It will suffice if the silicon component is that derived from a silicon compound, examples of which include elemental silicon as a metal (Si), a silicon oxide (SiO, $SiO_2$), a silicon alkoxide ($Si(OCH_3)_4$, $Si(OC_2H_5)_4$, $Si(OCH(CH_3)_2)_4$), a silicate (sodium silicate, potassium silicate), and an active silicate obtained by removing at least part of ions such as sodium ions and potassium ions from such silicate; there may be used one of them or a combination of two or more of them. Among them, it is preferred that there be used a silicate (sodium silicate) and an active silicate, particularly preferably an active silicate.

The silicon component (in terms of oxide) is preferably contained in an amount of 1 to 10,000, more preferably 2 to 5,000, even more preferably 5 to 1,000, in terms of a mass ratio to titanium oxide ($TiO_2/SiO_2$). This is because if the mass ratio is lower than 1, the photocatalytic effect may not be sufficiently exhibited as titanium oxide is now contained at a lower rate; and if the mass ratio is greater than 10,000, there may be observed an insufficient effect of inhibiting the agglutination and precipitation of titanium oxide.

In addition to the iron and silicon components, as a component for further enhancing photocatalytic activity, a titanium component may be used to surface-modify the titanium oxide particles. While the titanium component is for further enhancing the photocatalytic activity of the photocatalyst thin film, it will suffice if the titanium component is that derived from a titanium compound, examples of which include elemental titanium as a metal (Ti), a titanium hydroxide ($Ti(OH)_4$), a titanium oxyhydroxide ($TiO(OH)_2$), a titanium chloride ($TiCl_4$, $TiCl_3$, $TiCl_2$), a titanium nitrate ($Ti(NO)_4$), a titanium sulfate ($Ti(SO_4)_2$, $TiOSO_4$), a titanium halide (Br, I) other than a titanium chloride, and a titanium complex compound; there may be used one of them or a combination of two or more of them.

The titanium component (in terms of oxide) is preferably contained in an amount of 10 to 100,000, more preferably 20 to 10,000, even more preferably 50 to 1,000, in terms of a mass ratio to titanium oxide $(TiO)_2$ (titanium oxide particles)/$TiO_2$ (modifying component)). This is because if the mass ratio is lower than 10, titanium oxide will agglutinate and precipitate so that the quality of the photocatalyst thin film obtained will deteriorate, and the photocatalytic effect thereof may thus not be exerted in a sufficient manner; and if the mass ratio is greater than 100,000, there may be observed an insufficient effect of enhancing the activity.

As an aqueous dispersion medium of the titanium oxide particle dispersion liquid, while water is preferably used, there may also be used a mixed solvent of water and a hydrophilic organic solvent which is to be mixed with water at any ratio. As water, preferred are, for example, purified waters such as a filtrate water, a deionized water, a distilled water and a pure water. Moreover, as the hydrophilic organic solvent, preferred are, for example, alcohols such as methanol, ethanol and isopropanol; glycols such as ethylene glycol; and glycol ethers such as ethylene glycol monomethyl ether, ethylene glycol monoethyl ether and propylene glycol-n-propyl ether. If using such mixed solvent, it is preferred that a ratio of the hydrophilic organic solvent in the mixed solvent be larger than 0% by mass, but not larger than 50% by mass; more preferably larger than 0% by mass, but not larger than 20% by mass; even more preferably larger than 0% by mass, but not larger than 10% by mass.

The titanium oxide particles in the titanium oxide particle dispersion liquid, with tin and the visible light activity-enhancing transition metal component being solid-dissolved therein, and with the surfaces of the titanium oxide particles being modified by the iron and silicon components, preferably have a particle diameter of 3 to 50 nm, more preferably 3 to 40 nm, even more preferably 3 to 30 nm, the particle diameter being a 50% cumulative distribution diameter (possibly referred to as $D_{50}$ hereunder) on volumetric basis that is measured by a dynamic light scattering method using a laser light. This is because if $D_{50}$ is smaller than 3 nm, an insufficient photocatalytic activity may be observed; and if $D_{50}$ is greater than 50 nm, the dispersion liquid and the photocatalyst thin film obtained from such dispersion liquid may be opaque.

Further, as for a 90% cumulative distribution diameter (possibly referred to as $D_{90}$ hereunder) thereof on volumetric basis, it is preferred that such diameter be 5 to 100 nm, more preferably 5 to 80 nm, respectively. This is because if $D_{90}$ is smaller than 5 nm, an insufficient photocatalytic activity may be observed; and if $D_{90}$ is greater than 100 nm, the dispersion liquid and the photocatalyst thin film obtained from such dispersion liquid may be opaque.

It is preferable if the titanium oxide particles are particles whose $D_{50}$ and $D_{90}$ fall into the above ranges, because there can be obtained a dispersion liquid having a high photocatalytic activity and a high transparency; and a photocatalyst thin film produced from such dispersion liquid.

Here, as a device for measuring the $D_{50}$ and $D_{90}$ of the titanium oxide particles in the titanium oxide particle dispersion liquid, there may be used, for example, ELSZ-2000ZS (by Otsuka Electronics Co., Ltd.), NANOTRAC UPA-EX150 (by Nikkiso Co., Ltd.) or LA-910 (by HORIBA, Ltd.).

It is preferred that a concentration of the titanium oxide particles in the titanium oxide particle dispersion liquid be 0.01 to 20% by mass, particularly preferably 0.5 to 10% by mass, in terms of ease in producing a photocatalyst thin film having a given thickness.

(ii) Antimicrobial Metal-Containing Metal Particles

The metal particle component (ii) contained in the titanium oxide particle-metal particle dispersion liquid of the present invention is one comprised of a metal component containing at least one kind of antimicrobial property-enhancing metal component.

The term "antimicrobial property-enhancing metal component" refers to metal components that are harmful to microorganisms such as bacteria and molds, but are relatively less harmful to the human body; examples of such metal components include silver, copper, zinc, platinum, palladium, nickel, aluminum, titanium, cobalt, zirconium, molybdenum and tungsten that are known to reduce the viable count of *Staphylococcus aureus* and *E. coli* in a specification test for antimicrobial products JIS Z 2801 when used as metal component particles to coat a film. As the antimicrobial property-enhancing metal component, particularly preferable examples thereof include at least one kind of metal selected from silver, copper and zinc.

It is preferred that the metal particle component (ii) be added to the titanium oxide particle-metal particle dispersion liquid of the present invention as a metal particle dispersion liquid.

These antimicrobial property-enhancing metal components themselves or solutions thereof may be used by being added to the titanium oxide particles; however, as a result of adding a metal component itself or a solution thereof to titanium oxide particles that have already had their activity improved via surface modification, the effect of yielding an improved photocatalytic activity will be impaired. In order to avoid this, it is preferred that metal particles that are prepared separately be added to the titanium oxide particles, and it is more preferred that a protective agent be adsorbed onto the surfaces of these metal particles.

The metal particles are metal particles containing at least one kind of these metals, or may be alloy particles containing two or more kinds of these metals.

Examples of alloy particles include those comprised of combinations of metal components, such as silver-copper, silver-palladium, silver-platinum, silver-tin, gold-copper, silver-nickel, silver-antimony, silver-copper-tin, gold-copper-tin, silver-nickel-tin, silver-antimony-tin, platinum-manganese, silver-titanium, copper-tin, cobalt-copper, zinc-magnesium, silver-zinc, copper-zinc and silver-copper-zinc.

There are no particular restrictions on metal components in the metal particles other than the antimicrobial property-enhancing metal component(s); for example, there may be employed at least one selected from gold, antimony, tin, sodium, magnesium, silicon, potassium, calcium, scandium, vanadium, chromium, manganese, iron, gallium, germanium, arsenic, selenium, yttrium, niobium, technetium, ruthenium, rhodium, indium, tellurium, cesium, barium, hafnium, tantalum, rhenium, osmium, iridium, mercury, thallium, lead, bismuth, polonium, radium, lanthanum, cerium, praseodymium, neodymium, promethium, samarium, europium, gadolinium, actinium, and thorium.

The antimicrobial property-enhancing metal component (s) in the metal particles are contained in an amount of 1 to 100% by mass, preferably 10 to 100% by mass, more preferably 50 to 100% by mass, in terms of a ratio of the antimicrobial metal(s) to the total mass of the metal particles. This is because when the antimicrobial property-enhancing metal component(s) are in an amount of smaller than 1% by mass, an insufficient antimicrobial capability may be exhibited.

There are no particular restrictions on the protective agent of the metal particles so long as it is able to adsorb to and stabilize the surfaces of the metal particles, and prevent agglutination and growth of the metal particles reduced and precipitated as well as deterioration in the effect by the antimicrobial metal(s) to improve the photocatalytic activity of the iron and silicon components with which the titanium oxide particles are modified; there may be used an organic compound having a capability as a surfactant and a dispersant. Further, if the protective agent has a reducibility, it can also serve as a later-described reductant. As the protective agent of the metal particles, there may be selected at least one from, for example, a surfactant such as an anionic surfactant, a cationic surfactant, and a non-ionic surfactant; a water-soluble polymer compound such as polyvinylpyrrolidone, polyvinyl alcohol, polyethylene glycol, polyethyleneimine, polyethylene oxide, polysulfonic acid, polyacrylic acid, and methylcellulose; an aliphatic amine compound such as ethanolamine, diethanolamine, triethanolamine, and propanolamine; a primary amine compound such as butylamine, dibutylamine, hexylamine, cyclohexylamine, heptylamine, 3-butoxypropylamine, octylamine, nonylamine, decylamine, dodecylamine, hexadecylamine, oleylamine, and octadecylamine; a diamine compound such as N,N-dimethylethylenediamine and N—N-diethylethylenediamine; a sulfonic acid compound such as mercaptosulfonic acid and toluenesulfonic acid; a carboxylic acid compound such as mercaptoacetic acid, citric acid, stearic acid, and oleic acid; a bromide such as hexatrimethylammonium bromide, tetrabutylammonium bromide, dodecyltrimethylammonium bromide, and tetradecyltrimethylammonium bromide; an aliphatic thiol compound such as dodecanethiol; and polyphenols such as flavonoid and phenolic acid.

The protective agent is preferably contained in an amount of 0.01 to 100, more preferably 0.05 to 20, in terms of a mass ratio to the metal particles (metal particles/protective agent adsorbed onto surfaces of metal particles). This is because if the mass ratio is lower than 0.01, the antimicrobial effect may not be sufficiently exhibited as the metal particles are now contained at a lower rate; and if the mass ratio is greater than 100, the protective effect on the metal particles will be insufficient so that the metal particles may agglutinate and grow, and an impaired photocatalytic activity may be observed. The amount of the protective agent contained can be measured by a later-described method.

As an aqueous dispersion medium for the metal particle dispersion liquid, an aqueous solvent is normally used, and it is preferred that there be used water, a water-soluble organic solvent mixable with water, and a mixed solvent of water and a water-soluble organic solvent. As water, preferred are, for example, a deionized water, a distilled water, and a pure water. Further, examples of the water-soluble organic solvent include alcohols such as methanol, ethanol, n-propanol, 2-propanol, n-butanol, 2-butanol, tert-butanol, ethylene glycol, diethylene glycol and polyethylene glycol; glycol ethers such as ethylene glycol monomethyl ether, ethylene glycol monoethyl ether, ethylene glycol monobutyl ether, diethylene glycol monomethyl ether, diethylene glycol monoethyl ether, diethylene glycol monobutyl ether and propylene glycol-n-propyl ether; ketones such as acetone and methyl ethyl ketone; water-soluble nitrogen-containing compounds such as 2-pyrrolidone and N-methylpyrrolidone; and ethyl acetate. Any one of them may be used alone, or two or more of them may be used in combination.

As for the average particle diameter of the metal particles in the metal particle dispersion liquid, a 50% cumulative distribution diameter (D50) on volumetric basis that is measured by a dynamic light scattering method using a laser light is preferably not larger than 200 nm, more preferably not larger than 100 nm, even more preferably not larger than 70 nm. There are no particular restrictions on the lower limit of the average particle diameter, and theoretically, even those having the minimum particle diameter enabling antimicrobial property may be used. However, practically, it is preferred that the average particle diameter be not smaller than 1 nm. Further, it is not preferable when the average particle diameter is greater than 200 nm, because the dispersion liquid and the photocatalyst thin film obtained from such dispersion liquid may be opaque.

Further, a 90% cumulative distribution diameter ($D_{90}$) thereof on volumetric basis is preferably 1,000 nm, more preferably not larger than 500 nm, even more preferably not larger than 200 nm. While there are no particular restrictions on the lower limit of $D_{90}$, it is preferred that $D_{90}$ of the metal particles be not smaller than 1 nm in terms of practical use. Further, it is not preferable when $D_{90}$ is greater than 1,000 nm, because the dispersion liquid and the photocatalyst thin film obtained from such dispersion liquid may be opaque.

Here, as a device for measuring the average particle diameters, there may be used, for example, ELSZ-2000ZS (by Otsuka Electronics Co., Ltd.), NANOTRAC UPA-EX150 (by Nikkiso Co., Ltd.) or LA-910 (by HORIBA, Ltd.).

There are no particular restrictions on the concentration of the metal particles in the metal particle dispersion liquid. In general, the lower the concentration is, the better a dispersion stability is, and it is preferred that the concentration be 0.0001 to 10% by mass, more preferably 0.001 to 5% by mass, even more preferably 0.01 to 1% by mass. It is not preferable if the concentration is lower than 0.0001% by mass, because productivity will be impaired significantly.

Binder

Further, a binder may also be added to the titanium oxide particle-metal particle dispersion liquid for the purpose of making it easy to apply the dispersion liquid to the surfaces of later-described various members, and allow the particles to adhere thereto. Examples of the binder include metal compound-based binders containing silicon, aluminum, titanium, zirconium or the like; and organic resin-based binders containing an acrylic resin, a urethane resin or the like.

It is preferred that the binder be added and used in a manner such that a mass ratio between the binder and the titanium oxide and metal particles [titanium oxide particles+metal particles/binder] will fall into a range of 99 to 0.01, more preferably 9 to 0.1, even more preferably 2.5 to 0.4. This is because if the mass ratio is greater than 99, the titanium oxide particles may adhere to the surfaces of various members in an insufficient manner; and if the mass ratio is lower than 0.01, an insufficient photocatalytic activity may be observed.

Particularly, in order to obtain an excellent photocatalyst thin film having a high photocatalytic activity and transparency, it is preferred that a silicon compound-based binder be added and used in a manner such that the mass ratio (titanium oxide particles+metal particles/silicon compound-based binder) will fall into the range of 99 to 0.01, more preferably 9 to 0.1, even more preferably 2.5 to 0.4. Here, the silicon compound-based binder refers to a colloid dispersion liquid, solution or emulsion of a solid or liquid silicon compound capable of being contained in an aqueous dispersion medium, specific examples of which include a colloidal silica (preferable particle diameter 1 to 150 nm); solutions of silicate salts such as silicate; silane and siloxane hydrolysate emulsions; a silicone resin emulsion; and emulsions of copolymers of silicone resins and other resins, such as a silicone-acrylic resin copolymer and a silicone-urethane resin copolymer.

<Method for Producing Titanium Oxide Particle-Metal Particle Dispersion Liquid>

The titanium oxide particle-metal particle dispersion liquid of the present invention is obtained in such a state that dispersed in the aqueous dispersion medium are the two kinds of particles which are:

(i) the titanium oxide particles with the tin component and the visible light activity-enhancing transition metal component being solid-dissolved therein, and with the surfaces of the titanium oxide particles being modified by the iron component and the silicon component that are not solid-dissolved in the titanium oxide particles; and (ii) the antimicrobial metal-containing metal particles.

As a production method of such titanium oxide particle-metal particle dispersion liquid, there may be employed, for example, a method having the following steps (1) to (8).

(1) A step of producing a tin component and transition metal component-containing peroxotitanic acid solution from a raw material titanium compound, tin compound, transition metal compound, basic substance, hydrogen peroxide and aqueous dispersion medium.

(2) A step of obtaining a dispersion liquid of titanium oxide particles with the tin and transition metal components being solid-dissolved therein, by heating the tin component and transition metal component-containing peroxotitanic acid solution produced in the step (1) at 80 to 250° C. under a controlled pressure.

(3) A step of producing a solution or dispersion liquid of an iron component and a silicon component from an iron compound, silicon compound and aqueous dispersion medium.

(4) A step of obtaining a dispersion liquid of titanium oxide particles surface-modified by the iron and silicon components, by mixing the titanium oxide particle dispersion liquid produced in the step (2) and the solution or dispersion liquid of the iron and silicon components that has been produced in the step (3).

(5) A step of respectively producing a solution containing a raw material antimicrobial metal compound, and a solution containing a reductant for reducing such metal compound and a protective agent for coating and protecting metal particles.

(6) A step of producing a metal particle dispersion liquid by mixing the solutions obtained in the step (5) which are the solution containing the raw material antimicrobial metal compound, and the solution containing the reductant for reducing such metal compound and the protective agent for coating and protecting metal particles.

(7) A step of washing the metal particle dispersion liquid produced in the step (6) by a membrane filtration method, using an aqueous dispersion medium.

(8) A step of mixing the titanium oxide particle dispersion liquid obtained in the step (4) and the metal particle dispersion liquid obtained in the step (7).

The steps (1) to (4) are steps for producing the dispersion liquid of the titanium oxide particles with the tin component and the transition metal component being solid-dissolved therein, and with the surfaces of the titanium oxide particles being modified by the iron component and the silicon component.

The steps (5) to (7) are steps for producing the metal particle dispersion liquid. While there are various physical and chemical methods, these production steps particularly employ a liquid phase reduction method which is a chemical method having advantages in terms of ease in adjusting synthesis conditions, wider controllable ranges of, for example, composition, particle diameter and particle diameter distribution, and productivity. In such liquid phase reduction method, the metal particles are to be precipitated by mixing the reductant into the solution containing metal ions as raw materials. At that time, by allowing the protective agent of the metal particles to coexist in the reaction system, there can be more easily realized, for example, improving the dispersibility of the metal particles in the solvent, controlling their particle diameters, and inhibiting a deterioration in photocatalytic activity when mixed with the titanium oxide particles.

The step (8) is a step for finally producing the titanium oxide particle-metal particle dispersion liquid by mixing: the liquid obtained in the step (4) which is the dispersion liquid of the titanium oxide particles with the tin and transition metal components being solid-dissolved therein, and with the surfaces of the titanium oxide particles being modified by the iron and silicon components; and the liquid obtained in the step (7) which is the antimicrobial metal-containing metal particle dispersion liquid.

Each step is described in detail hereunder.

<Method for Producing Dispersion Liquid of Titanium Oxide Particles with Tin Component and Transition Metal Component being Solid-Dissolved Therein, and with Particle Surfaces being Modified by Iron Component and Silicon Component>

The dispersion liquid of the titanium oxide particles with the tin and transition metal components being solid-dissolved therein, and with the particle surfaces being modified by the iron and silicon components, is produced by separately producing a dispersion liquid of titanium oxide particles with the tin and transition metal components being solid-dissolved therein, and a solution or dispersion liquid of the iron and silicon components, and then mixing such dispersion liquid of the titanium oxide particles with the tin and transition metal components being solid-dissolved therein and the solution or dispersion liquid of the iron and silicon components.

As a method for producing the dispersion liquid of the titanium oxide particles with the tin and transition metal components being solid-dissolved therein, and with the particle surfaces being modified by the iron and silicon components, there may be specifically listed a production method having the following steps (1) to (4).

(1) A step of producing a tin component and transition metal component-containing peroxotitanic acid solution from a raw material titanium compound, tin compound, transition metal compound, basic substance, hydrogen peroxide and aqueous dispersion medium.

(2) A step of obtaining a titanium oxide particle dispersion liquid by heating the tin component and transition metal component-containing peroxotitanic acid solution produced in the step (1) at 80 to 250° C.' under a controlled pressure.

(3) A step of producing a solution or dispersion liquid of an iron component and a silicon component from an iron compound, silicon compound and aqueous dispersion medium.

(4) A step of obtaining a dispersion liquid of titanium oxide particles surface-modified by the iron and silicon components, by mixing the liquid produced in the step (2) which is the dispersion liquid of the titanium oxide particles with the tin and transition metal components being solid-dissolved therein, and the liquid produced in the step (3) which is the solution or dispersion liquid of the iron and silicon components.

Here, if further modifying the surfaces of the titanium oxide particles with the titanium component to further enhance the photocatalytic activity of the photocatalyst thin film, there can be obtained a dispersion liquid of titanium oxide particles surface-modified by the iron, silicon and titanium components in a similar manner as above except that a titanium compound is further added in the step (3).

The steps (1) to (2) are steps for obtaining the dispersion liquid of the titanium oxide particles with the tin and transition metal components being solid-dissolved therein; the step (3) is a step for obtaining the solution or dispersion liquid of the iron and silicon components; and the step (4) is a step for obtaining the dispersion liquid containing the titanium oxide particles with the tin and transition metal components being solid-dissolved therein, and with the particle surfaces being modified by the iron and silicon components.

Step (1):

In the step (1), the tin component and transition metal component-containing peroxotitanic acid solution is produced by reacting the raw material titanium compound, tin compound, transition metal compound, basic substance and hydrogen peroxide in the aqueous dispersion medium.

As a reaction method, there may be employed any of the following methods (i) to (iii).

(i) A method where the tin compound and transition metal compound are added and dissolved with respect to the raw material titanium compound and basic substance in the aqueous dispersion medium to obtain a tin component and transition metal component-containing titanium hydroxide, followed by removing impurity ions other than metal ions to be contained, and then adding hydrogen peroxide to obtain a tin component and transition metal component-containing peroxotitanic acid.

(ii) A method where the basic substance is added to the raw material titanium compound in the aqueous dispersion medium to obtain a titanium hydroxide, impurity ions other than metal ions to be contained are then removed, followed by adding the tin compound and transition metal compound, and then adding hydrogen peroxide to obtain a tin component and transition metal component-containing peroxotitanic acid.

(iii) A method where the basic substance is added to the raw material titanium compound in the aqueous dispersion medium to obtain a titanium hydroxide, impurity ions other than metal ions to be contained are then removed, hydrogen peroxide is then added to obtain a peroxotitanic acid, followed by adding the tin compound and transition metal compound to obtain a tin component and transition metal component-containing peroxotitanic acid.

Here, in the first part of the description of the method (i), "the raw material titanium compound and basic substance in the aqueous dispersion medium" may be prepared as two separate liquids of aqueous dispersion media such as "an aqueous dispersion medium with the raw material titanium compound dispersed therein" and "an aqueous dispersion medium with the basic substance dispersed therein," and each of the tin compound and transition metal compound may then be dissolved in one or both of these two liquids in accordance with the solubility of each of the tin compound and transition metal compound in these two liquids before mixing the two.

In this way, after obtaining the tin component and transition metal component-containing peroxotitanic acid, by subjecting such peroxotitanic acid to a later-described hydrothermal reaction in the step (2), there can be obtained titanium oxide particles with the various metals solid-dissolved in titanium oxide.

Here, examples of the raw material titanium compound include titanium chlorides; inorganic acid salts of titanium, such as titanium nitrate and titanium sulfate; organic acid salts of titanium, such as titanium formate, titanium citrate, titanium oxalate, titanium lactate and titanium glycolate; and titanium hydroxides precipitated by hydrolysis reactions as a result of adding alkalis to aqueous solutions of these chlorides and salts. There may be used one of them or a combination of two or more of them. Particularly, it is preferred that titanium chlorides ($TiCl_3$, $TiCl_4$) be used.

As for each of the tin compound, transition metal compound and aqueous dispersion medium, those described above are used at the compositions described above. Here, it is preferred that a concentration of a raw material titanium compound aqueous solution composed of the raw material titanium compound and aqueous dispersion medium be not higher than 60% by mass, particularly preferably not higher than 30% by mass. A lower limit of the concentration is appropriately determined; it is preferred that the lower limit be not lower than 1% by mass in general.

The basic substance is to smoothly turn the raw material titanium compound into a titanium hydroxide, examples of which include hydroxides of alkali metals or alkaline earth metals, such as sodium hydroxide and potassium hydroxide; and amine compounds such as ammonia, alkanolamine and alkylamine. Among these examples, it is particularly preferred that ammonia be used and be used in such an amount that the pH level of the raw material titanium compound aqueous solution will be 7 or higher, particularly 7 to 10. Here, the basic substance, together with the aqueous dispersion medium, may be turned into an aqueous solution having a proper concentration before use.

Hydrogen peroxide is to convert the raw material titanium compound or titanium hydroxide into a peroxotitanic acid i.e. a titanium oxide compound having a Ti—O—O—Ti bond, and is normally used in the form of a hydrogen peroxide water. It is preferred that hydrogen peroxide be added in an amount of 1.5 to 20 times the molar amount of the substance amount of Ti, or a total substance amount of Ti, the transition metal and Sn. Further, in the reaction where hydrogen peroxide is added to turn the raw material titanium compound or titanium hydroxide into the peroxotitanic acid, it is preferred that a reaction temperature be 5 to 80° C., and that a reaction time be 30 min to 24 hours.

The tin component and transition metal component-containing peroxotitanic acid solution thus obtained may also contain an alkaline substance or acidic substance for the purpose of pH adjustment or the like. Here, examples of the alkaline substance include ammonia, sodium hydroxide, calcium hydroxide and alkylamine; examples of the acidic substance include inorganic acids such as sulfuric acid, nitric acid, hydrochloric acid, carbonic acid, phosphoric acid and hydrogen peroxide, and organic acids such as formic acid, citric acid, oxalic acid, lactic acid and glycolic acid. In this case, it is preferred that pH of the peroxotitanic acid solution obtained be 1 to 9, particularly preferably 4 to 7, in terms of safety in handling.

Step (2):

In the step (2), the tin component and transition metal component-containing peroxotitanic acid solution obtained in the step (1) is subjected to a hydrothermal reaction under a controlled pressure and at a temperature of 80 to 250° C., preferably 100 to 250° C. for 0.01 to 24 hours. An appropriate reaction temperature is 80 to 250° C. in terms of reaction efficiency and reaction controllability; as a result, the tin component and transition metal component-containing peroxotitanic acid will be converted into titanium oxide particles with the tin component and the transition metal component being solid-dissolved therein. Here, the expression "under a controlled pressure" refers to a condition where if the reaction temperature is greater than the boiling point of the dispersion medium, a pressure will be applied in a proper manner such that the reaction temperature will be maintained; and even a condition where if the reaction temperature is not higher than the boiling point of the dispersion medium, atmospheric pressure will be used for control. The pressure employed here is normally about 0.12 to 4.5 MPa, preferably about 0.15 to 4.5 MPa, more preferably about 0.20 to 4.5 MPa. The reaction time is preferably 1 min to 24 hours. By this step (2), there can be obtained the dispersion liquid of the titanium oxide particles with the tin component and the transition metal component being solid-dissolved therein.

The pH of the dispersion liquid of the titanium oxide particles with the tin component and the transition metal component being solid-dissolved therein, which is obtained in the step (2), is preferably 7 to 14, more preferably 9 to 14. The dispersion liquid of the titanium oxide particles with the tin component and the transition metal component being solid-dissolved therein, which is obtained in the step (2), may also contain an alkaline substance or acidic substance for the purpose of pH adjustment or the like such that the dispersion liquid will have the abovementioned pH; the alkaline substance and acidic substance as well as a method for adjusting pH are similar to those in the case of the tin component and transition metal component-containing peroxotitanic acid solution obtained in the step (1).

It is preferred that the particle diameter ($D_{50}$ and $D_{90}$) of the titanium oxide particles obtained here fall into the ranges described above; the particle diameter can be controlled by adjusting the reaction condition(s), for example, the particle diameter can be made smaller by shortening the reaction time and a temperature rise time.

Step (3):

In the step (3), the solution or dispersion liquid of the iron and silicon components is produced by dissolving or dispersing a raw material iron compound and a raw material silicon compound in the aqueous dispersion medium, separately from the steps (1) and (2).

As the raw material iron compound, there may be listed the abovementioned iron compounds such as elemental iron as a metal (Fe), an iron oxide ($Fe_2O_3$, $Fe_3O_4$), an iron hydroxide ($Fe(OH)_2$, $Fe(OH)_3$), an iron oxyhydroxide (FeO (OH)), an iron chloride ($FeCl_2$, $FeCl_3$), an iron nitrate ($Fe(NO)_3$), an iron sulfate ($FeSO_4$, $Fe_2(SO_4)_3$), an iron halide (Br, I) other than an iron chloride, and an iron complex compound; there may be used one of them or a combination of two or more of them. Particularly, it is preferred that there be used an iron oxide ($Fe_2O_3$, $Fe_3O_4$), an iron oxyhydroxide (FeO(OH)), an iron chloride ($FeCl_2$, $FeCl_3$), an iron nitrate ($Fe(NO)_3$), and an iron sulfate ($FeSO_4$, $Fe_2(SO_4)_3$).

As the raw material silicon compound, there may be listed the abovementioned silicon compounds such as elemental silicon as a metal (Si), a silicon oxide (SiO, $SiO_2$), a silicon alkoxide ($Si(OCH_3)_4$, $Si(OC_2H_5)_4$, $Si(OCH(CH_3)_2)_4$), a silicate (sodium silicate, potassium silicate), and an active silicate obtained by removing ions such as sodium ions and potassium ions from such silicate; there may be used one of them or a combination of two or more of them. Particularly, it is preferred that there be used a silicate (sodium silicate) and an active silicate. An active silicate may for example be obtained by adding a cation-exchange resin to a sodium silicate aqueous solution prepared by dissolving sodium silicate in a pure water, and therefore removing at least part of the sodium ions; it is preferred that the cation-exchange resin be added in such a manner that an active silicate solution obtained will have a pH of 2 to 10, preferably 2 to 7.

The iron component and silicon component-containing solution or dispersion liquid thus obtained may also contain an alkaline substance or acidic substance for the purpose of pH adjustment or the like. These alkaline substance and acidic substance may employ those similar to the ones described above, and pH adjustment here may be carried out in a similar manner as above.

The iron component and silicon component-containing solution or dispersion liquid preferably has a pH of 1 to 7, more preferably 1 to 5.

In the solution or dispersion liquid of the iron and silicon components that is produced in the step (3), the concentration of the raw material iron compound is preferably 0.001 to 10% by mass, more preferably 0.01 to 5% by mass; and the concentration of the raw material silicon compound is preferably 0.001 to 10% by mass, more preferably 0.01 to 5% by mass.

Further, a titanium component may further be dissolved or dispersed in this solution or dispersion liquid of the iron and silicon components.

If a titanium component is to be contained, a raw material titanium compound may be any of the titanium compounds listed above such as elemental titanium as a metal (Ti), a titanium hydroxide ($Ti(OH)_4$), a titanium oxyhydroxide ($TiO(OH)_2$), a titanium chloride ($TiCl_4$, $TiCl_3$, $TiCl_2$), a titanium nitrate ($Ti(NO)_4$), a titanium sulfate ($Ti(SO_4)_2$, $TiOSO_4$), a titanium halide (Br, I) other than a titanium chloride, a titanium complex compound, and a peroxotitanium compound (a titanium oxide compound having a Ti—O—O—Ti bond); there may be used one of them or a combination of two or more of them. Particularly, it is preferred that there be used a titanium hydroxide ($Ti(OH)_4$), a titanium oxyhydroxide ($TiO(OH)_2$), a titanium chloride ($TiCl_4$, $TiCl_3$, $TiCl_2$), a titanium nitrate ($Ti(NO)_4$), a titanium sulfate ($Ti(SO_4)_2$, $TiOSO_4$), and a peroxotitanium compound (a titanium oxide compound having a Ti—O—O—Ti bond).

Step (4):

In the step (4), the titanium oxide particle dispersion liquid that has been obtained in the step (2) and the solution or dispersion liquid of the iron and silicon components that has been obtained in the step (3) are mixed. No particular restrictions are imposed on a mixing method; there may be used a method of performing stirring with a stirrer, or a method of performing dispersion with an ultrasonic disperser. A temperature at the time of mixing is 20 to 100° C., preferably 20 to 80° C., more preferably 20 to 40° ° C. A mixing time is preferably 1 min to 3 hours. In terms of a mixing ratio, mixing may be performed in such a manner that the mass ratios between $TiO_2$ and Fe, Si in terms of oxide ($Fe_2O_3$ and $SiO_2$) in the titanium oxide particle dispersion liquid shall be the above-described mass ratios.

The titanium oxide particle dispersion liquid obtained by the steps (1) to (4) may also contain an alkaline substance or acidic substance for the purpose of pH adjustment or the like; as a pH adjuster, there may be used those described above. Further, an ion-exchange treatment and a filtration washing treatment may be performed to adjust the concentration of ion components, or a solvent replacement treatment may be performed to change the solvent component.

The titanium oxide particle dispersion liquid preferably has a pH of 7 to 14, more preferably 8 to 12.

The mass of the titanium oxide particles contained in the titanium oxide particle dispersion liquid can be calculated from the mass and concentration of the titanium oxide particle dispersion liquid. Here, a method for measuring the concentration of the titanium oxide particle dispersion liquid is such that part of the titanium oxide particle dispersion liquid is sampled, and the concentration is then calculated with the following formula based on the mass of a non-volatile content (titanium oxide particles) after volatilizing the solvent by performing heating at 105° C. for 1 hour and the mass of the titanium oxide particle dispersion liquid sampled.

$$\text{Concentration of titanium oxide particle dispersion liquid (\%)} = [\text{mass of non-volatile content (g)} / \text{mass of titanium oxide particle dispersion liquid (g)}] \times 100$$

<Method for Producing Antimicrobial Metal-Containing Metal Particle Dispersion Liquid>

In a method for producing the antimicrobial metal-containing metal particle dispersion liquid, the antimicrobial metal-containing metal particle dispersion liquid is produced in such a manner that the metal particle dispersion liquid obtained by mixing the antimicrobial metal compound-containing solution with the reductant and protective agent-containing solution is subjected to membrane filtration to have components other than the metal particles removed for purification.

As the method for producing the antimicrobial metal-containing metal particle dispersion liquid, there may be specifically listed a production method having the following steps (5) to (7).

(5) A step of respectively producing a solution containing a raw material antimicrobial metal compound, and a solution containing a reductant for reducing such metal compound and a protective agent for coating and protecting metal particles.

(6) A step of producing a metal particle dispersion liquid by mixing the solutions obtained in the step (5) which are the solution containing the raw material antimicrobial metal compound, and the solution containing the reductant for reducing such metal compound and the protective agent for coating and protecting metal particles.

(7) A step of washing the metal particle dispersion liquid produced in the step (6) by a membrane filtration method, using an aqueous dispersion medium.

Here, if the metal particles are intended to be alloy particles composed of multiple kinds of metal, there can be obtained an alloy particle dispersion liquid composed of multiple kinds of metal in a similar manner except that a metal compound(s) is further added to the raw material antimicrobial metal compound-containing solution in the step (5).

Step (5):

In the step (5), there are produced a solution with the raw material antimicrobial metal compound being dissolved in an aqueous dispersion medium; and a solution with the reductant for reducing such raw material antimicrobial metal compound being dissolved in an aqueous dispersion medium.

As a method for producing these solutions, there may be employed a method in which each of the raw material antimicrobial metal compound and the reductant for reducing such raw material antimicrobial metal compound is separately added into an aqueous dispersion medium so as to be dissolved therein by performing stirring. There are no particular restrictions on a stirring method so long as it is a method capable of realizing a uniform dissolution in the aqueous dispersion medium; there may be used a stirrer that is generally available.

Various antimicrobial metal compounds may be used as the raw material antimicrobial metal compound, examples of which include antimicrobial metal chlorides; inorganic acid salts such as nitrates and sulfates; organic acid salts such as formic acid, citric acid, oxalic acid, lactic acid and glycolic acid; and complex salts such as amine complex, cyano complex, halogeno complex and hydroxy complex. Any one of them may be used alone, or two or more of them may be used in combination. Particularly, it is preferred that chlorides and inorganic acid salts such as nitrates and sulfates be used.

There are no particular restrictions on the reductant; there can be used any kind of reductant capable of reducing the metal ions composing the raw material antimicrobial metal compound. Examples of the reductant include hydrazines such as hydrazine, hydrazine monohydrate, phenylhydrazine and hydrazinium sulfate; amines such as dimethylamino-ethanol triethylamine, octylamine, dimethylaminoborane and benzotriazole; organic acids such as citric acid, ascorbic acid, tartaric acid, malic acid, malonic acid and formic acid; hydrides such as sodium borohydride, lithium borohydride, lithium triethylborohydride, lithium aluminum hydride, diisobutylaluminum hydride, tributyltin hydride, lithium tri (sec-butyl)borohydride, potassium tri(sec-butyl)borohydride, zinc borohydride and acetoxy sodium borohydride; pyrrolidones such as polyvinylpyrrolidone, 1-vinylpyrrolidone, N-vinylpyrrolidone and methylpyrrolidone; reducing sugars such as glucose, galactose, mannose, fructose, sucrose, maltose, raffinose and stachyose; and sugar alcohols such as sorbitol. Any one of them may be used alone, or two or more of them may be used in combination. As the aqueous dispersion medium for dissolving the reductant, there may be used an aqueous dispersion medium similar to the one used for the metal compound.

A protective agent may be added to the solution with the reductant being dissolved in the aqueous dispersion medium. It is preferred that the protective agent(s) descried above be contained at the abovementioned mass ratios.

As the aqueous dispersion medium (aqueous solvent), those described above are preferably used.

A basic substance or an acidic substance may be added to the solvent. Examples of such basic substance include alkali metal hydroxides such as sodium hydroxide and potassium hydroxide; alkali metal carbonates such as sodium carbonate and potassium carbonate; alkali metal hydrogen carbonates such as sodium hydrogen carbonate and potassium hydrogen carbonate; alkali metal alkoxides such as potassium tert-butoxide, sodium methoxide and sodium ethoxide; alkali metal salts of aliphatic hydrocarbons such as butyl lithium; and amines such as triethylamine, diethylaminoethanol and diethylamine. Examples of the acidic substance include inorganic acids such as aqua regia, hydrochloric acid, nitric acid and sulfuric acid; and organic acids such as formic acid, acetic acid, chloroacetic acid, dichloroacetic acid, oxalic acid, trifluoroacetic acid and trichloroacetic acid.

There are no particular restrictions on the concentrations of these two solutions; it is preferred that the concentrations be set to preferable ranges in accordance with the range of a target primary particle diameter as there is a tendency where in general, the lower the concentrations are, the more likely the primary particle diameter of each metal particle formed can be made small.

There are no particular restrictions on the pH of these two solutions; it is preferred that pH be favorably adjusted in accordance with, for example, a target molar ratio of the metal(s) in the metal particles or a target primary particle diameter thereof.

Step (6):

In the step (6), the metal particle dispersion liquid is produced by mixing the solutions prepared in the step (5) which are the solution with the raw material antimicrobial metal compound being dissolved in an aqueous dispersion medium, and the solution with the reductant for reducing such raw material antimicrobial metal compound being dissolved in an aqueous dispersion medium.

There are no particular restrictions on a method for mixing these two solutions, as long as the method employed allows the two solutions to be uniformly mixed together. For example, there may be employed a method where the metal compound solution and the reductant solution are put into a reaction container before being stirred and mixed together; a method where stirring and mixing is performed in a way such that the reductant solution is delivered by drops into the metal compound solution already placed in a reaction container while stirring such metal compound solution; a method where stirring and mixing is performed in a way such that the metal compound solution is delivered by drops into the reductant solution already placed in a reaction container while stirring such reductant solution; or a method where the metal compound solution and the reductant solution are continuously supplied in constant amounts such that a reaction container or a flow reactor, for example, may then be used to perform mixing.

There are no particular restrictions on a temperature at the time of preforming mixing; it is preferred that the temperature be adjusted to a preferable temperature based on, for example, a target primary particle diameter or a reaction time.

Step (7):

In the step (7), the metal particle dispersion liquid produced in the step (6) is washed with an aqueous dispersion medium by a membrane filtration method.

As the aqueous dispersion medium, it is preferred that there be used water, a water-soluble organic solvent mixable with water, or a mixed solvent of water and a water-soluble organic solvent. As water, preferred are, for example, a deionized water, a distilled water and a pure water. Further, examples of the water-soluble organic solvent include alcohols such as methanol, ethanol, isopropanol, n-propanol, 2-propanol, n-butanol, 2-butanol, tert-butanol, ethylene glycol and diethylene glycol; glycol ethers such as ethylene glycol monomethyl ether, ethylene glycol monoethyl ether, ethylene glycol monobutyl ether, diethylene glycol monomethyl ether, diethylene glycol monoethyl ether, diethylene glycol monobutyl ether and propylene glycol-n-propyl ether; ketones such as acetone and methyl ethyl ketone; water-soluble nitrogen-containing compounds such as 2-pyrrolidone and N-methylpyrrolidone; and ethyl acetate. As the water-soluble organic solvent, any one of them may be used alone, or two or more of them may be used in combination.

By performing a membrane filtration method, unwanted non-volatile content other than the metal particles can be washed away and separated from the metal particle dispersion liquid; examples of such non-volatile content include components other than metals in the raw material metal compound, the reductant, and an excess amount of the protective agent that is not adsorbed onto the surfaces of the metal particles. It is preferred that in this step, components other than the metal particles and the protective agent adsorbed onto the surfaces thereof are separated from the metal particle dispersion liquid.

It is preferred that washing be repeatedly performed until a mass ratio between the metal particles with the protective agent being adsorbed onto the surfaces thereof and non-volatile content other than these metal particles in the metal particle dispersion liquid (metal particles with protective agent being adsorbed onto surfaces thereof/non-volatile content other than these metal particles) has become not smaller than 1, more preferably not smaller than 10, even more preferably not smaller than 100. This is because a mass ratio smaller than 1 indicates a lower content ratio of the metal particles, which may cause the antimicrobial effect to be exerted in an insufficient manner.

Determination of Metal Component Concentration in Metal Particle Dispersion Liquid (ICP-OES)

The metal component (metal particle) concentration C (% by mass) in the metal particle dispersion liquid can be measured by appropriately diluting the metal particle dispersion liquid with a pure water, and then introducing the diluted liquid into an inductively coupled plasma optical emission spectrometer (product name "Agilent 5110 ICP-OES" by Agilent Technologies, Inc.).

Determination of Metal Particles with Protective Agent being Adsorbed onto Surfaces Thereof in Metal Particle Dispersion Liquid A mass $M_2$ (g) of the metal particles with the protective agent being adsorbed onto the surfaces thereof can be calculated as follows.

At first, the metal particle dispersion liquid is sampled to measure a mass $M_1$ (g) thereof. Next, the metal particle dispersion liquid of the mass $M_1$ (g) is heated at 105° C. for 3 hours to volatilize the solvent and then measure a mass $M_a$ (g) of the non-volatile content. A mass S (g) of the solvent volatilized at that time is: mass S (g)=$M_1$ (g)−$M_a$ (g). Further, the non-volatile content of the mass $M_a$ (g) is dispersed in and washed by a pure water, followed by precipitating, via centrifugal separation, the metal particles with the protective agent being adsorbed onto the surfaces thereof, and thereby removing a supernatant containing a non-volatile content $M_3$ (g) other than the metal particles with the protective agent being adsorbed onto the surfaces thereof. This operation was repeated five times, and the precipitate obtained (the metal particles with the protective agent being adsorbed onto their surfaces) is further heated at 105° C. for 3 hours and then cooled before having its mass $M_2$ (g) measured.

Mass $M_2$ (g) of metal particles with protective agent being adsorbed onto their surfaces=Mass $M_1$ (g) of metal particle dispersion liquid sampled−Solvent $S$ (g)−Non-volatile content $M_3$ (g) other than metal particles with protective agent being adsorbed onto their surfaces Determination of Protective Agent Adsorbed onto Surfaces of Metal Particles A mass $M_4$ (g) of the protective agent adsorbed onto the surfaces of the metal particles can be calculated from the obtained metal component concentration C (% by mass), mass $M_1$ (g) of the metal particle dispersion liquid sampled, and mass $M_2$ (g) of the metal particles with the protective agent being adsorbed onto the surfaces thereof.

Mass $M_4$ (g) of protective agent adsorbed onto surfaces of metal particles=Mass $M_2$ (g) of metal particles with protective agent being adsorbed onto their surfaces−[Mass $M_1$ (g) of metal particle dispersion liquid sampled×Metal component concentration $C$ (% by mass)÷100]

Determination of Non-Volatile Content Other than Metal Particles with Protective Agent being Adsorbed onto Surfaces Thereof in Metal Particle Dispersion Liquid The mass $M_3$ (g) of the non-volatile content other than the metal particles with the protective agent being adsorbed onto the surfaces thereof can be calculated from the obtained mass $M_1$ (g) of the metal particle dispersion liquid sampled, mass S (g) of the solvent, and mass $M_2$ (g) of the metal particles with the protective agent being adsorbed onto the surfaces thereof.

Mass $M_3$ (g) of non-volatile content other than metal particles with protective agent being adsorbed onto their surfaces=Mass $M_1$ (g) of metal particle dispersion liquid sampled−Mass $S$ (g) of solvent−Mass $M_2$ (g) of metal particles with protective agent being adsorbed onto their surfaces.

There are no particular restrictions on a membrane used in the membrane filtration method, as long as the membrane used is capable of separating, from the metal particle dispersion liquid, the metal particles with the protective agent being adsorbed onto the surfaces thereof, and the non-volatile content other than these metal particles. Examples of such membrane include a microfiltration membrane, an ultrafiltration membrane and a nanofiltration membrane. Among these membranes, filtration can be carried out using a membrane having a suitable pore size.

As a filtration method, there may also be employed any of, for example, centrifugal filtration, pressure filtration and cross-flow filtration.

As for the shape of the filtration membrane, there may be appropriately employed those of, for example, a hollow-fiber type, a spiral type, a tubular type or a flat membrane type.

There are no particular restrictions on the material of the filtration membrane, as long as the material employed has a durability against the metal particle dispersion liquid. The material may be appropriately selected from, for example, organic films such as those made of polyethylene, tetrafluoroethylene, polypropylene, cellulose acetate, polyacrylonitrile, polyimide, polysulfone and polyether sulfone; and inorganic films such as those made of silica, alumina, zirconia and titania.

Specific examples of the abovementioned filtration membrane include microza (by Asahi Kasei Chemicals Corporation), Amicon Ultra (by Merck Millipore Corporation), Ultra filter (by Advantec Toyo Kaisha, Ltd.), MEMBRALOX (by Nihon Pall Ltd.), and Cefilt (by NGK INSULATORS, LTD.).

Step (8):

In the step (8), the titanium oxide particle-metal particle dispersion liquid is obtained by mixing the dispersion liquids obtained in the steps (4) and (7) which are respectively: the dispersion liquid of the titanium oxide particles with the tin and transition metal components being solid-dissolved therein, and with the surfaces of the titanium oxide particles being modified by the iron and silicon components; and the antimicrobial metal-containing metal particle dispersion liquid.

There are no particular restrictions on a mixing method, as long as the method employed allows the two kinds of dispersion liquids to be uniformly mixed together; for example, mixing may be carried out by performing stirring using a commonly available stirrer.

A mixing ratio between the titanium oxide particle dispersion liquid and the metal particle dispersion liquid is 1 to 100,000, preferably 10 to 10,000, even more preferably 100 to 1,000, in terms of a particle mass ratio between the titanium oxide particles and the metal particles in each dispersion liquid (titanium oxide particles/metal particles). It is not preferable when the mass ratio is lower than 1, because the photocatalytic property will not be fully exhibited; it is also not preferable when the mass ratio is greater than 100,000, because the antimicrobial capability will not be fully exhibited.

As for the dispersion particle diameter of the mixture of the titanium oxide particles and metal particles in the titanium oxide particle-metal particle dispersion liquid, i.e., a 50% cumulative distribution diameter ($D_{50}$) (also referred to as "average particle diameter") on volumetric basis that is measured by a dynamic light scattering method using a laser light, the dispersion particle diameter is as above.

Further, a device for measuring the average particle diameter is as above as well.

As described above, a total concentration of the titanium oxide particles, metal particles and non-volatile content other than these particles in the titanium oxide particle-metal particle dispersion liquid thus prepared is preferably 0.01 to 20% by mass, particularly preferably 0.5 to 10% by mass, in terms of ease in producing a photocatalyst thin film having a given thickness. As for concentration adjustment, if the concentration is higher than a desired concentration, it can be lowered by diluting the dispersion liquid by adding an aqueous solvent thereto; if the concentration is lower than a desired concentration, it can be raised by volatilizing or filtrating away the aqueous solvent.

Here, a method for measuring the concentration of the titanium oxide particle-metal particle dispersion liquid is such that part of the titanium oxide particle-metal particle dispersion liquid is sampled, followed by heating the same at 105° C. for 3 hours to volatilize the solvent, whereby the concentration can then be calculated based on the mass of the non-volatile content (titanium oxide particles, metal particles, and non-volatile impurities) and the mass of the sampled titanium oxide particle-metal particle dispersion liquid, using the following formula.

Concentration of titanium oxide particle-metal particle dispersion liquid (%)=[Mass of non-volatile content (g)/Mass of titanium oxide particle-metal particle dispersion liquid (g)]×100

Further, if adding the abovementioned binder improving film formability, it is preferred that a solution of the binder (aqueous binder solution) be added to the titanium oxide particle-metal particle dispersion liquid that has already had its concentration adjusted as above, in such a manner that a desired concentration will be achieved after mixing Here, the silicon component contained in the titanium oxide particle dispersion liquid is to inhibit the agglutination and precipitation of the titanium oxide particles and the iron component, and inhibit deterioration in photocatalytic activity; the silicon component is simultaneously added when mixing the titanium oxide particles and the iron component. In contrast, the binder is to improve the film formability of the titanium oxide particle-metal particle dispersion liquid, and is added in a time period from after producing the titanium oxide particle-metal particle dispersion liquid until applying the same, which makes the binder different from the silicon component.

Next, described is an embodiment in which the titanium oxide particle-metal particle composition of the present invention is in the form of a titanium oxide particle-metal particle thin film.

The titanium oxide particle-metal particle dispersion liquid, which is one embodiment of the present invention, can be used to form photocatalyst thin films on the surfaces of various members. Here, the various members are not particularly limited; examples of materials for these members may include organic materials and inorganic materials. These can have various shapes according to their respective purposes and uses.

Examples of organic materials include synthetic resin materials such as a vinyl chloride resin (PVC), polyethylene (PE), polypropylene (PP), polycarbonate (PC), acrylic resin, polyacetal, fluororesin, silicone resin, ethylene-vinyl acetate copolymer (EVA), acrylonitrile-butadiene rubber (NBR), polyethylene terephthalate (PET), polyethylene naphthalate (PEN), polyvinyl butyral (PVB), ethylene-vinyl alcohol copolymer (EVOH), polyimide resin, polyphenylene sulfide (PPS), polyetherimide (PEI), polyetheretherimide (PEEI), polyetheretherketone (PEEK), melamine resin, phenolic resin, and acrylonitrile-butadiene-styrene (ABS) resin; natural materials such as a natural rubber; or semisynthetic materials of the above synthetic resin materials and natural materials. These may be manufactured into products having given shapes and configurations, such as films, sheets, fiber materials, fiber products, other molded products, and laminates.

Examples of inorganic materials include non-metallic inorganic materials and metallic inorganic materials. Examples of nonmetallic inorganic materials include glass, ceramics, and stone materials. These may be manufactured into products having various shapes, such as tiles, glass, mirrors, walls, and design materials. Examples of metallic inorganic materials include cast iron, steel materials, iron, iron alloys, aluminum, aluminum alloys, nickel, nickel alloys, and zinc die-cast. These may be plated with the aforementioned metallic inorganic materials, coated with the aforementioned organic materials, or used to plate the surfaces of the aforementioned organic materials or non-metallic inorganic materials.

The titanium oxide particle-metal particle dispersion liquid of the present invention is particularly useful for forming photocatalyst thin films by being applied to various members made of inorganic substances such as glass and metals, and organic substances such as resins, and is especially useful for forming transparent photocatalyst thin films on various members.

As a method for forming photocatalyst thin films on the surfaces of various members, for example, the titanium oxide particle-metal particle dispersion liquid may be applied to the surface of such member by a known coating method such as spray coating or dip coating, followed by performing drying via a known drying method such as far-infrared drying, IH drying, or hot air drying. The thickness of the photocatalyst thin film may be selected variously; normally, the thickness is preferably 10 nm to 10 μm.

In this way, the titanium oxide particle-metal particle thin film is formed. In this case, if the dispersion liquid contains a binder of the amount described above, there will be formed a thin film containing the titanium oxide particles, the metal particles and the binder.

In addition to being transparent and yielding a favorable photocatalytic action in lights of the ultraviolet region (wavelength 10 to 400 nm) as are the conventional cases, the photocatalyst thin film thus formed can also provide a more excellent photocatalytic action even in lights of the visible region (wavelength 400 to 800 nm) in which a sufficient photocatalytic action was unable to be achieved with the conventional photocatalysts; due to the antimicrobial action of the metal particles and the photocatalytic action of the titanium oxide, various members on which this photocatalyst thin film is formed can exhibit effects such as a cleaning, a deodorizing, and an antimicrobial effect on the surfaces thereof.

WORKING EXAMPLES

The present invention is described in detail hereunder with reference to working and comparative examples. However, the present invention is not limited to the following working examples. Various measurements in the present invention were performed as follows.

(1) 50% and 90% Cumulative Distribution Diameters of Titanium Oxide Particles and/or Metal Particles in Dispersion Liquid ($D_{50}$ and $D_{90}$)

$D_{50}$ and $D_{90}$ of the titanium oxide particles and metal particles in the dispersion liquid were calculated as 50% and 90% cumulative distribution diameters on volumetric basis that are measured by a dynamic light scattering method using a laser light, by means of a particle diameter distribution measurement device (ELSZ-2000ZS by Otsuka Electronics Co., Ltd.).

(2) Acetaldehyde Gas Decomposition Capability Test of Photocatalyst Thin Film

The activity of a photocatalyst thin film produced by applying the dispersion liquid and then drying the same was evaluated through a decomposition reaction of an acetaldehyde gas. The evaluation was performed by a batch-wise gas decomposition capability evaluation method.

Using a #7 wire bar coater, each titanium oxide particle dispersion liquid prepared in the working or comparative examples was applied to and spread on the entire surface of an A4-sized PET film (210 mm×297 mm) in a way such that a dry mass of the titanium oxide particles and metal particles would be about 20 mg. A sample thus prepared was then dried in an oven of 80° C. for 1 hour to obtain an evaluation sample for acetaldehyde gas decomposition capability evaluation.

Using such evaluation sample, the photocatalytic activity of the titanium oxide particles and metal particles was evaluated via a decomposition reaction of acetaldehyde gas. The evaluation was performed by a batch-wise gas decomposition capability evaluation method.

Specifically, the evaluation sample was at first placed into a 5 L stainless cell equipped with a quartz glass window. This cell was then filled with an acetaldehyde gas having an initial concentration with a humidity thereof being controlled to 50%, followed by performing light irradiation with a light source provided at an upper portion of the cell. As a result of having the acetaldehyde gas decomposed by the photocatalytic action of titanium oxide, the acetaldehyde gas concentration in the cell will decrease. There, by measuring a change in the concentration, the intensity of photocatalytic activity can be confirmed. The acetaldehyde gas concentration was measured by a photoacoustic multi-gas monitor (product name "INNOVA1412" by LumaSense Technologies), and the photocatalytic activity was evaluated by measuring a time it took for the acetaldehyde gas concentration to reach 1 ppm or lower after the light irradiation was initiated. The shorter the time measured is, the higher the photocatalytic activity is; the longer the time measured is, the lower the photocatalytic activity is.

In a photocatalytic activity evaluation under visible light irradiation, an LED (product model number "TH-211×200SW" by CCS Inc., spectral distribution: 400 to 800 nm) was used as a light source, and visible light irradiation was carried out at an illuminance of 10,000 lx. At that time, the initial concentration of the acetaldehyde in the cell was set to 5 ppm.

Each test result was evaluated based on the following criteria.

Very favorable (indicated as ◎) . . . Decreased within 5 hours

Favorable (indicated as ○) . . . Decreased within 10 hours

Slightly unfavorable (indicated as Δ) . . . Decreased within 20 hours

Unfavorable (indicated as x) . . . Failed to decrease within 20 hours (3) Antimicrobial Property Test of Photocatalyst Thin Film (Dark Place, Under Visible Light Irradiation)

The antimicrobial capability of the photocatalyst thin film was tested using a sample prepared by applying the photocatalyst thin film to a 50 mm-squared glass base material so that the thickness of the film would be 100 nm, where with regard to an antimicrobial capability under visible light irradiation, the antimicrobial capability was tested by a testing method in accordance with a method for testing a hybrid photocatalyst antimicrobial-treated plate product, as described in "Fine ceramics (advanced ceramics, advanced technical ceramics)—Test method for antibacterial activity of photocatalytic materials and efficacy under indoor lighting environment" of Japanese Industrial Standards JIS R 1752:2020. A sharp cut filter of Type B was used, and illuminance was set to 3,000 lx.

Each test result was evaluated based on the following criteria.

Very favorable (indicated as ◎) . . . All antimicrobial activity values were not lower than 4.0.

Favorable (indicated as ○) . . . All antimicrobial activity values were not lower than 2.0.

Unfavorable (indicated as x) . . . Some antimicrobial activity values were lower than 2.0.

(4) Identification of Crystal Phase of Titanium Oxide Particles

The crystal phase of the titanium oxide particles was identified in a way where the dispersion liquid of the titanium oxide particles obtained was dried at 105° C. for three hours to obtain a titanium oxide particle powder, followed by collecting the titanium oxide particle powder so as to subject the same to powder X-ray diffraction analysis, using a diffraction device (product name "Benchtop X-ray diffractometer D2 PHASER" by BRUKER AXS Co., Ltd.).

(5) Preparation of Titanium Oxide Particle Dispersion Liquid

Preparation Example 1-1

<Preparation of Titanium Oxide Particle Dispersion Liquid>

<Preparation of Dispersion Liquid of Titanium Oxide Particles with Tin and Molybdenum Solid-Dissolved Therein>

Tin (IV) chloride was added to and dissolved in a 36% by mass titanium (IV) chloride aqueous solution so that $TiO_2$/Sn (molar ratio) in a titanium oxide particle dispersion liquid obtained would be 20, followed by diluting the solution thus prepared 10 times with a pure water, and then neutralizing and hydrolyzing the same by gradually adding a 10% by mass ammonia water, thereby obtaining a precipitate of a tin-containing titanium hydroxide. pH at that time was 8. The precipitate thus obtained was then deionized by repeating the addition of pure water and decantation. Sodium molybdate (VI) was then added to the deionized precipitate of the tin-containing titanium hydroxide so that $TiO_2$/Mo (molar ratio) in the titanium oxide particle dispersion liquid obtained would be 400. A 35% by mass hydrogen peroxide water was further added so that $H_2O_2$/(Ti+Sn+Mo) (molar ratio) therein would be 10, followed by performing stirring at 60° C. for two hours so as to sufficiently react the solution, thereby obtaining an orange transparent tin and molybdenum-containing peroxotitanic acid solution (1a).

Next, 400 mL of the tin and molybdenum-containing peroxotitanic acid solution (1a) was put into a 500 ml autoclave so as to be subjected to a hydrothermal treatment at 150° C. for 90 min, followed by adding a pure water to adjust the concentration thereof, thereby obtaining a dispersion liquid (1A) of titanium oxide particles with tin and molybdenum solid-dissolved therein (titanium oxide concentration 1.2% by mass). As a result of performing powder X-ray diffraction analysis on the titanium oxide particles, there were only observed peaks of a rutile-type titanium oxide; it was confirmed that tin and molybdenum were solid-dissolved in titanium oxide.

Preparation Example 1-2

<Preparation of Dispersion Liquid of Titanium Oxide Particles with Tin and Tungsten Solid-Dissolved Therein>

Tin (IV) chloride was added to and dissolved in a 36% by mass titanium (IV) chloride aqueous solution so that $TiO_2$/Sn (molar ratio) in a titanium oxide particle dispersion liquid obtained would be 10, followed by diluting the solution thus prepared 10 times with a pure water, and then neutralizing and hydrolyzing the same by gradually adding a 10% by mass ammonia water, thereby obtaining a precipitate of a tin-containing titanium hydroxide. pH at that time was 8. The precipitate thus obtained was then deionized by repeating the addition of pure water and decantation. Sodium tungstate (VI) was then added to the deionized precipitate of the tin-containing titanium hydroxide so that $TiO_2$/W (molar ratio) in the titanium oxide particle dispersion liquid obtained would be 100. A 35% by mass hydrogen peroxide water was further added so that $H_2O_2$/(Ti+Sn+W) (molar ratio) therein would be 10, followed by performing stirring at 60° C. for two hours so as to sufficiently react the solution, thereby obtaining an orange transparent tin and tungsten-containing peroxotitanic acid solution (1b).

Next, 400 mL of the tin and tungsten-containing peroxotitanic acid solution (1b) was put into a 500 mL autoclave so as to be subjected to a hydrothermal treatment at 160° C. for 60 min, followed by adding a pure water to adjust the concentration thereof, thereby obtaining a dispersion liquid (1B) of titanium oxide particles with tin and tungsten solid-dissolved therein (titanium oxide concentration 1.2% by mass). As a result of performing powder X-ray diffraction analysis on the titanium oxide particles, there were only observed peaks of a rutile-type titanium oxide; it was confirmed that tin and tungsten were solid-dissolved in titanium oxide.

Preparation Example 1-3

<Preparation of Dispersion Liquid of Titanium Oxide Particles with Tin and Vanadium Solid-Dissolved Therein>

Tin (IV) chloride was added to and dissolved in a 36% by mass titanium (IV) chloride aqueous solution so that $TiO_2$/Sn (molar ratio) in a titanium oxide particle dispersion liquid obtained would be 33, followed by diluting the solution thus prepared 10 times with a pure water, and then neutralizing and hydrolyzing the same by gradually adding a 10% by mass ammonia water, thereby obtaining a precipitate of a tin-containing titanium hydroxide. pH at that time was 8. The precipitate thus obtained was then deionized by repeating the addition of pure water and decantation. Sodium vanadate (V) was then added to the deionized precipitate of the tin-containing titanium hydroxide so that $TiO_2$/V (molar ratio) in the titanium oxide particle dispersion liquid obtained would be 2,000. A 35% by mass hydrogen peroxide water was further added so that $H_2O_2$/(Ti+Sn+V) (molar ratio) therein would be 10, followed by performing stirring at 50° C. for three hours so as to sufficiently react the solution, thereby obtaining an orange transparent tin and vanadium-containing peroxotitanic acid solution (le).

Next, 400 mL of the tin and vanadium-containing peroxotitanic acid solution (1c) was put into a 500 mL autoclave so as to be subjected to a hydrothermal treatment at 140° C. for 120 min, followed by adding a pure water to adjust the concentration thereof, thereby obtaining a dispersion liquid (1C) of titanium oxide particles with tin and vanadium solid-dissolved therein (titanium oxide concentration 1.2% by mass). As a result of performing powder X-ray diffraction analysis on the titanium oxide particles, there were only observed peaks of an anatase-type titanium oxide and a rutile-type titanium oxide; it was confirmed that tin and vanadium were solid-dissolved in titanium oxide.

Preparation Example 1-4

<Preparation of Dispersion Liquid of Titanium Oxide Particles with Tin and Molybdenum Solid-Dissolved Therein>

Tin (IV) chloride was added to and dissolved in a 36% by mass titanium (IV) chloride aqueous solution so that $TiO_2$/Sn (molar ratio) in a titanium oxide particle dispersion liquid obtained would be 20, followed by diluting the solution thus prepared 10 times with a pure water, and then neutralizing and hydrolyzing the same by gradually adding a 10% by mass ammonia water, thereby obtaining a precipitate of a tin-containing titanium hydroxide. pH at that time was 8. The precipitate thus obtained was then deionized by repeating the addition of pure water and decantation. Sodium molybdate (VI) was then added to the deionized precipitate of the tin-containing titanium hydroxide so that $TiO_2$/Mo (molar ratio) in the titanium oxide particle dispersion liquid obtained would be 100. A 35% by mass hydrogen peroxide water was further added so that $H_2O_2$/(Ti+Sn+Mo) (molar ratio) therein would be 12, followed by performing stirring at 60° C. for two hours so as to sufficiently react the solution, thereby obtaining an orange transparent tin and molybdenum-containing peroxotitanic acid solution (1d).

Next, 400 mL of the tin and molybdenum-containing peroxotitanic acid solution (d) was put into a 500 mL autoclave so as to be subjected to a hydrothermal treatment at 120° C. for 180 min, followed by adding a pure water to adjust the concentration thereof, thereby obtaining a dispersion liquid (1D) of titanium oxide particles with tin and molybdenum solid-dissolved therein (titanium oxide concentration 1.2% by mass). As a result of performing powder X-ray diffraction analysis on the titanium oxide particles, there were only observed peaks of a rutile-type titanium oxide; it was confirmed that tin and molybdenum were solid-dissolved in titanium oxide.

Preparation Example 1-5

<Preparation of Dispersion Liquid of Titanium Oxide Particles with Tin Solid-Dissolved Therein>

A dispersion liquid (1E) of titanium oxide particles with tin solid-dissolved therein (titanium oxide concentration 1.2% by mass) was obtained in a similar manner as the preparation example 1-1, except that sodium molybdate (VI) was not added. As a result of performing powder X-ray diffraction analysis on the titanium oxide particles, there were only observed peaks of a rutile-type titanium oxide; it was confirmed that tin was solid-dissolved in titanium oxide.

Preparation Example 1-6

<Preparation of Dispersion Liquid of Titanium Oxide Particles with Molybdenum Solid-Dissolved Therein>

A dispersion liquid (1F) of titanium oxide particles with molybdenum solid-dissolved therein (titanium oxide concentration 1.2% by mass) was obtained in a similar manner as the preparation example 1-1, except that tin (IV) chloride was not added. As a result of performing powder X-ray diffraction analysis on the titanium oxide particles, there were only observed peaks of an anatase-type titanium oxide; it was confirmed that molybdenum was solid-dissolved in titanium oxide.

Preparation Example 1-7

<Preparation of Dispersion Liquid of Titanium Oxide Particles with Tungsten Solid-Dissolved Therein>

A dispersion liquid (1G) of titanium oxide particles with tungsten solid-dissolved therein (titanium oxide concentration 1.2% by mass) was obtained in a similar manner as the preparation example 1-2, except that tin (IV) chloride was not added. As a result of performing powder X-ray diffraction analysis on the titanium oxide particles, there were only observed peaks of an anatase-type titanium oxide; it was confirmed that tungsten was solid-dissolved in titanium oxide.

Preparation Example 1-8

<Preparation of Dispersion Liquid of Titanium Oxide Particles with Vanadium Solid-Dissolved Therein>

A dispersion liquid (1H) of titanium oxide particles with vanadium solid-dissolved therein (titanium oxide concentration 1.2% by mass) was obtained in a similar manner as the preparation example 1-3, except that tin (IV) chloride was not added. As a result of performing powder X-ray diffraction analysis on the titanium oxide particles, there were only observed peaks of an anatase-type titanium oxide; it was confirmed that vanadium was solid-dissolved in titanium oxide.

Preparation Example 1-9

<Preparation of Titanium Oxide Particle Dispersion Liquid>

By diluting a 36% by mass titanium (IV) chloride aqueous solution 10 times with a pure water, and then by neutralizing and hydrolyzing the same by gradually adding a 10% by mass ammonia water, a precipitate of a titanium hydroxide was obtained. pH at that time was 8.5. The precipitate thus obtained was then deionized by repeating the addition of pure water and decantation. A 35% by mass hydrogen peroxide water was further added to the deionized precipitate of the titanium hydroxide so that $H_2O_2$/Ti (molar ratio) would be 8, followed by performing stirring at 60° C. for two hours so as to sufficiently react the solution, thereby obtaining an orange transparent peroxotitanic acid solution (li).

Next, 400 mL of the peroxotitanic acid solution (li) was put into a 500 mL autoclave so as to be subjected to a hydrothermal treatment at 130° C. for 90 min, followed by adding a pure water to adjust the concentration thereof, thereby obtaining a dispersion liquid (1I) of titanium oxide particles (titanium oxide concentration 1.2% by mass). As a result of performing powder X-ray diffraction analysis on the titanium oxide particles, there were only observed peaks of an anatase-type titanium oxide.

Shown collectively in Table I are the molar ratios, hydrothermal treatment conditions and dispersion particle diameters ($D_{50}$, $D_{90}$) of the titanium oxide particles prepared in each preparation example as well as pH of the corresponding titanium oxide particle dispersion liquids after the hydrothermal treatment. The dispersion particle diameters were measured by a dynamic light scattering method using a laser light (ELSZ-2000ZS by Otsuka Electronics Co., Ltd.).

TABLE 1

| Preparation example | Titanium oxide particle dispersion liquid | Molar ratio $TiO_2$/Sn | $TiO_2$/Mo | $TiO_2$/W | $TiO_2$/V | Hydrothermal treatment Temperature ° C. | Time min | Dispersion particle diameter nm $D_{50}$ | $D_{90}$ | pH |
|---|---|---|---|---|---|---|---|---|---|---|
| 1-1 | 1A | 20 | 400 | — | — | 150 | 90 | 8 | 14 | 10.5 |
| 1-2 | 1B | 10 | — | 100 | — | 160 | 60 | 7 | 13 | 10.2 |
| 1-3 | 1C | 33 | — | — | 2000 | 140 | 120 | 13 | 28 | 10.6 |
| 1-4 | 1D | 20 | 100 | — | — | 120 | 180 | 11 | 24 | 10.7 |
| 1-5 | 1E | 20 | — | — | — | 150 | 90 | 13 | 26 | 10.5 |
| 1-6 | 1F | — | 400 | — | — | 150 | 90 | 18 | 26 | 10.5 |
| 1-7 | 1G | — | — | 100 | — | 160 | 60 | 20 | 39 | 10.2 |
| 1-8 | 1H | — | — | — | 2000 | 140 | 120 | 19 | 37 | 10.6 |
| 1-9 | 1I | — | — | — | — | 130 | 90 | 18 | 37 | 10.5 |

(6) Preparation of Dispersion Liquid of Surface-Modified Titanium Oxide Particles Preparation Example 2-1

<Preparation of Dispersion Liquid of Titanium Oxide Particles Surface-Modified by Iron and Silicon Components>

A strongly acidic cation-exchange resin (AmberLite HPR1024H by ORGANO CORPORATION) was added to and stirred with a silicate soda aqueous solution obtained by dissolving 0.34 g of JIS No. 3 silicate soda (29.1% by mass in terms of $SiO_2$) into 100 g of a pure water, after which an active silicate aqueous solution was obtained by filtrating away the ion-exchange resin. By adding 0.31 g of a 41% iron (III) sulfate aqueous solution to this active silicate aqueous solution, there was obtained an aqueous solution of iron sulfate and active silicate having a pH of 2.4.

After using a stirrer to mix the above-obtained aqueous solution of iron sulfate and active silicate with the titanium oxide particle dispersion liquid (1A) at 25° C. for an hour so that $TiO_2/Fe_2O_3$ would be 200 and $TiO_2/SiO_2$ would be 100, a solid content concentration was then adjusted to 1% by mass with a pure water to obtain a dispersion liquid (2A) of titanium oxide particles surface-modified by iron and silicon components.

Preparation Example 2-2

<Preparation of Dispersion Liquid of Titanium Oxide Particles Surface-Modified by Iron and Silicon Components>

A dispersion liquid (2B) of titanium oxide particles surface-modified by iron and silicon components was obtained in a similar manner as the preparation example 2-1, except that the titanium oxide particle dispersion liquid (1B) was used.

Preparation Example 2-3

<Preparation of Dispersion Liquid of Titanium Oxide Particles Surface-Modified by Iron and Silicon Components>

A dispersion liquid (2C) of titanium oxide particles surface-modified by iron and silicon components was obtained in a similar manner as the preparation example 2-1, except that the titanium oxide particle dispersion liquid (1C) was used.

Preparation Example 2-4

<Preparation of Dispersion Liquid of Titanium Oxide Particles Surface-Modified by Iron, Titanium and Silicon Components>

A strongly acidic cation-exchange resin (AmberLite HPR1024H by ORGANO CORPORATION) was added to and stirred with a silicate soda aqueous solution obtained by dissolving 1.71 g of JIS No. 3 silicate soda (29.1% in terms of $SiO_2$) into 100 g of a pure water, after which an active silicate aqueous solution was obtained by filtrating away the ion-exchange resin. By adding 0.31 g of a 41% iron (III) sulfate aqueous solution and 0.33 g of a 36% titanium (IV) chloride aqueous solution to this active silicate aqueous solution, there was obtained an aqueous solution of iron sulfate, titanium chloride and active silicate having a pH of 1.6.

After using a stirrer to mix the above-obtained aqueous solution of iron sulfate, titanium chloride and active silicate with the titanium oxide particle dispersion liquid (1A) at 25° C. for an hour so that $TiO_2/Fe_2O_3$ would be 200, $TiO_2/TiO_2$ (modification component) would be 200, and $TiO_2/SiO_2$ would be 20, a solid content concentration was then adjusted to 1% by mass with a pure water to obtain a dispersion liquid (2D) of titanium oxide particles surface-modified by iron, titanium and silicon components.

Preparation Example 2-5

<Preparation of Dispersion Liquid of Titanium Oxide Particles Surface-Modified by Iron and Silicon Components>

A strongly acidic cation-exchange resin (AmberLite HPR1024H by ORGANO CORPORATION) was added to and stirred with a silicate soda aqueous solution obtained by dissolving 0.17 g of JIS No. 3 silicate soda (29.1% by mass in terms of $SiO_2$) into 100 g of a pure water, after which an active silicate aqueous solution was obtained by filtrating away the ion-exchange resin. By adding 0.15 g of a 41% iron (III) sulfate aqueous solution to this active silicate aqueous solution, there was obtained an aqueous solution of iron sulfate and active silicate having a pH of 2.6.

After using a stirrer to mix the above-obtained aqueous solution of iron sulfate and active silicate with the titanium oxide particle dispersion liquid (1D) at 25° C. for an hour so that $TiO_2/Fe_2O_3$ would be 400 and $TiO_2/SiO_2$ would be 200, a solid content concentration was then adjusted to 1% by mass with a pure water to obtain a dispersion liquid (2E) of titanium oxide particles surface-modified by iron and silicon components.

Preparation Example 2-6

<Preparation of Dispersion Liquid of Titanium Oxide Particles Surface-Modified by Iron and Silicon Components>

A dispersion liquid (2F) of titanium oxide particles surface-modified by iron and silicon components was obtained in a similar manner as the preparation example 2-1, except that the titanium oxide particle dispersion liquid (1E) was used.

Preparation Example 2-7

<Preparation of Dispersion Liquid of Titanium Oxide Particles Surface-Modified by Iron and Silicon Components>

A dispersion liquid (2G) of titanium oxide particles surface-modified by iron and silicon components was obtained in a similar manner as the preparation example 2-1, except that the titanium oxide particle dispersion liquid (1F) was used.

Preparation Example 2-8

<Preparation of Dispersion Liquid of Titanium Oxide Particles Surface-Modified by Iron and Silicon Components>

A dispersion liquid (2H) of titanium oxide particles surface-modified by iron and silicon components was obtained in a similar manner as the preparation example 2-1, except that the titanium oxide particle dispersion liquid (1G) was used.

Preparation Example 2-9

<Preparation of Dispersion Liquid of Titanium Oxide Particles Surface-Modified by Iron and Silicon Components>

A dispersion liquid (2I) of titanium oxide particles surface-modified by iron and silicon components was obtained in a similar manner as the preparation example 2-1, except that the titanium oxide particle dispersion liquid (1H) was used.

Preparation Example 2-10

<Preparation of Dispersion Liquid of Titanium Oxide Particles Surface-Modified by Iron and Silicon Components>

A dispersion liquid (2J) of titanium oxide particles surface-modified by iron and silicon components was obtained in a similar manner as the preparation example 2-1, except that the titanium oxide particle dispersion liquid (1I) was used.

Preparation Example 2-11

<Preparation of Dispersion Liquid of Titanium Oxide Particles Surface-Modified by Silicon Component>

An active silicate aqueous solution having a pH of 4.8 was obtained in a similar manner as the preparation example 2-1, except that iron (III) sulfate was not added.

After using a stirrer to mix the above-obtained active silicate aqueous solution with the titanium oxide particle dispersion liquid (1A) at 25° C. for an hour so that $TiO_2$/

$SiO_2$ would be 100, a solid content concentration was then adjusted to 1% by mass with a pure water to obtain a dispersion liquid (2K) of titanium oxide particles surface-modified by a silicon component.

Preparation Example 2-12

<Preparation of Dispersion Liquid of Titanium Oxide Particles Surface-Modified by Iron Component>

An aqueous solution of iron sulfate having a pH of 2.4 was obtained by adding 0.31 g of a 41% iron (III) sulfate aqueous solution to 100 g of a pure water and stirring them.

After using a stirrer to mix the above-obtained aqueous solution of iron sulfate with the dispersion liquid of the titanium oxide particles (1A) at 25° C. for an hour so that $TiO_2/Fe_2O_3$ would be 200, a solid content concentration was then adjusted to 1% by mass with a pure water to obtain a dispersion liquid (2L) of titanium oxide particles surface-modified by an iron component. While adding the aqueous solution of iron sulfate, the dispersion liquid exhibited white turbidity, and precipitation was partially observed therein.

Kasei Chemicals Corporation) and washing the liquid with a pure water. The metal particle dispersion liquids obtained are summarized in Table 3.

Preparation Example 3-2

<Preparation of Silver and Copper Particle Dispersion Liquid>

A raw material metal compound-containing solution was obtained by dissolving silver nitrate and copper nitrate dihydrate in ethylene glycol as a solvent so that a concentration in terms of Ag would be 2.50 mmol/L and a concentration in terms of Cu would be 2.50 mmol/L.

A reductant-containing solution was obtained by mixing 55% by mass of ethylene glycol and 8% by mass of a pure water as solvents; 2% by mass of potassium hydroxide as a basic substance; 20% by mass of a hydrazine hydrate and 5% by mass of dimethylaminoethanol as reductants; and 10% by mass of polyvinylpyrrolidone as a reductant and protective agent.

A silver and copper particle dispersion liquid (3B) was obtained by mixing 0.2 L of the reductant-containing solution of 25° C. into 2 L of the raw material metal compound-containing solution that had been heated to 150° C. in a reactor, and then concentrating the liquid thus obtained with the aid of an ultrafiltration membrane having a molecular weight cut-off of 10,000 (microza by Asahi Kasei Chemicals Corporation) and washing the liquid with a pure water.

TABLE 2

| Preparation example | Titanium oxide particle dispersion liquid | Surface-modified titanium oxide particle dispersion liquid | Mass ratio of surface modifying omponents to TIO2 in titanium oxide particle dispersion liquid excluding components solid-dissolved in titanium oxide) | | | Dispersion particle diameter nm | | pH |
|---|---|---|---|---|---|---|---|---|
| | | | $TiO_2/Fe_2O_3$ | $TiO_2/TiO_2$ | $TiO_2/SiO_2$ | $D_{50}$ | $D_{90}$ | |
| 2-1 | 1A | 2A | 200 | 0 | 100 | 12 | 21 | 10.2 |
| 2-2 | 1B | 2B | 200 | 0 | 100 | 11 | 20 | 9.8 |
| 2-3 | 1C | 2C | 200 | 0 | 100 | 20 | 41 | 10.3 |
| 2-4 | 1A | 2D | 200 | 200 | 20 | 14 | 25 | 10.3 |
| 2-5 | 1D | 2E | 400 | 0 | 200 | 15 | 32 | 10.4 |
| 2-6 | 1E | 2F | 200 | 0 | 100 | 15 | 33 | 10.2 |
| 2-7 | 1F | 2G | 200 | 0 | 100 | 27 | 40 | 10.2 |
| 2-8 | 1G | 2H | 200 | 0 | 100 | 29 | 65 | 10.0 |
| 2-9 | 1H | 2I | 200 | 0 | 100 | 30 | 56 | 10.2 |
| 2-10 | 1I | 2J | 200 | 0 | 100 | 21 | 40 | 10.3 |
| 2-11 | 1A | 2K | 0 | 0 | 100 | 10 | 18 | 10.4 |
| 2-12 | 1A | 2L | 200 | 0 | 0 | 56 | 138 | 10.2 |

(7) Preparation of Metal Particle Dispersion Liquid

Preparation Example 3-1

<Preparation of Silver Particle Dispersion Liquid>

A raw material metal compound-containing solution was obtained by dissolving silver nitrate in ethylene glycol as a solvent so that a concentration in terms of Ag would be 2.50 mmol/L.

A reductant-containing solution was obtained by mixing 55% by mass of ethylene glycol and 8% by mass of a pure water as solvents; 2% by mass of potassium hydroxide as a basic substance; 20% by mass of a hydrazine hydrate and 5% by mass of dimethylaminoethanol as reductants; and 10% by mass of polyvinylpyrrolidone as a reductant and protective agent.

A silver particle dispersion liquid (3A) was obtained by mixing 0.2 L of the reductant and protective agent-containing solution of 25° C. into 2 L of the raw material metal compound-containing solution that had been heated to 90° C. in a reactor, and then concentrating the liquid thus obtained with the aid of an ultrafiltration membrane having a molecular weight cut-off of 10,000 (microza by Asahi Preparation Example 3-3

<Preparation of Silver and Zinc Particle Dispersion Liquid>

A silver and zinc particle dispersion liquid (3C) was obtained in a similar manner as the preparation example 3-2, except that there was used a raw material metal compound-containing solution obtained by dissolving silver nitrate and zinc nitrate hexahydrate in ethylene glycol as a solvent so that a concentration in terms of Ag would be 3.75 mmol/L and a concentration in terms of Zn would be 1.25 mmol/L.

Preparation Example 3-4

<Preparation of Silver Particle Dispersion Liquid>

A silver particle dispersion liquid (3D) was obtained in a similar manner as the preparation example 3-1, except that the amount of pure water used for washing by the ultrafiltration membrane was reduced.

Preparation Example 3-5

<Preparation of Silver Particle Dispersion Liquid>

A silver particle dispersion liquid (3E) was obtained in a similar manner as the preparation example 3-1, except that polyvinylpyrrolidone as a reductant and protective agent was not added.

TABLE 3

| Preparation example | Metal particle dispersion liquid | Metallic species: Metal component 1 | Metallic species: Metal component 2 | Mass ratio: Metal particles/Protactive agent adsorbed onto metal particle surfaces | Mass ratio: Metal particles with protective agent adsorbed onto surfaces thereof/non-volatile content other than these metal particles | Dispersion particle diameter nm: $D_{50}$ | Dispersion particle diameter nm: $D_{90}$ |
|---|---|---|---|---|---|---|---|
| 3-1 | 3A | Ag | — | 0.15 | 150 | 43 | 53 |
| 3-2 | 3B | Ag | Cu | 0.16 | 300 | 55 | 72 |
| 3-3 | 3C | Ag | Zn | 0.12 | 250 | 67 | 93 |
| 3-4 | 3D | Ag | — | 0.15 | 1 | 50 | 65 |
| 3-5 | 3E | Ag | — | — | — | 180 | 461 |

(8) Preparation of Titanium Oxide Particle-Metal Particle Dispersion Liquid

Working Example 1

A titanium oxide particle-metal particle dispersion liquid (E-1) of the present invention was obtained by mixing the surface-protected metal particle dispersion liquid (3A) into the surface-modified titanium oxide particle dispersion liquid (2A) so that a mass ratio of the particles contained in each dispersion liquid (surface-modified titanium oxide particles/surface-protected metal particles) would be 100. The titanium oxide particle-metal particle dispersion liquids obtained are summarized in Table 4.

Working Example 2

A titanium oxide particle-metal particle dispersion liquid (E-2) of the present invention was obtained by mixing the surface-protected metal particle dispersion liquid (3B) into the surface-modified titanium oxide particle dispersion liquid (2B) so that a mass ratio of the particles contained in each dispersion liquid (surface-modified titanium oxide particles/surface-protected metal particles) would be 400.

Working Example 3

A titanium oxide particle-metal particle dispersion liquid (E-3) of the present invention was obtained by mixing the surface-protected metal particle dispersion liquid (3C) into the surface-modified titanium oxide particle dispersion liquid (2C) so that a mass ratio of the particles contained in each dispersion liquid (surface-modified titanium oxide particles/surface-protected metal particles) would be 200.

Working Example 4

A titanium oxide particle-metal particle dispersion liquid (E-4) of the present invention was obtained by mixing the surface-protected metal particle dispersion liquid (3A) into the surface-modified titanium oxide particle dispersion liquid (2D) so that a mass ratio of the particles contained in each dispersion liquid (surface-modified titanium oxide particles/surface-protected metal particles) would be 100.

Working Example 5

A titanium oxide particle-metal particle dispersion liquid (E-5) of the present invention was obtained by mixing the surface-protected metal particle dispersion liquid (3A) into the surface-modified titanium oxide particle dispersion liquid (2E) so that a mass ratio of the particles contained in each dispersion liquid (surface-modified titanium oxide particles/surface-protected metal particles) would be 100.

Working Example 6

A titanium oxide particle-metal particle dispersion liquid (E-6) of the present invention was obtained by mixing the surface-protected metal particle dispersion liquid (3D) into the surface-modified titanium oxide particle dispersion liquid (2A) so that a mass ratio of the particles contained in each dispersion liquid (surface-modified titanium oxide particles/surface-protected metal particles) would be 100.

Working Example 7

A titanium oxide particle-metal particle dispersion liquid (E-7) of the present invention was obtained by mixing the metal particle dispersion liquid (3E) into the surface-modified titanium oxide particle dispersion liquid (2A) so that a mass ratio of the particles contained in each dispersion liquid (surface-modified titanium oxide particles/metal particles) would be 1,000.

Working Example 8

A binder-containing titanium oxide particle dispersion liquid (E-8) was obtained by adding a silicon compound-based (silica-based) binder (colloidal silica, product name: SNOWTEX 20 by Nissan Chemical Corporation) into the titanium oxide particle-metal particle dispersion liquid (E-1) so that titanium oxide and metal particles/binder (mass ratio) would be 1.5, and mixing them at 25° C. for 10 min using a stirrer. The binder-containing titanium oxide particle-metal particle dispersion liquids are summarized in Table 5.

Comparative Example 1

A titanium oxide particle dispersion liquid (C-1) for use in comparative evaluation was obtained from the surface-modified titanium oxide particle dispersion liquid (2A).

Comparative Example 2

A metal particle dispersion liquid (C-2) for use in comparative evaluation was obtained from the surface-protected silver particle dispersion liquid (3A).

Comparative Example 3

A titanium oxide particle-metal particle dispersion liquid (C-3) for use in comparative evaluation was obtained by mixing the surface-protected metal particle dispersion liquid (3A) into the titanium oxide particle dispersion liquid (1A) so that a mass ratio of the particles contained in each dispersion liquid (titanium oxide particles/surface-protected metal particles) would be 100.

Comparative Example 4

A titanium oxide particle-metal particle dispersion liquid (C-4) for use in comparative evaluation was obtained by mixing the surface-protected metal particle dispersion liquid (3A) into the surface-modified titanium oxide particle dispersion liquid (2F) so that a mass ratio of the particles contained in each dispersion liquid (surface-modified titanium oxide particles/surface-protected metal particles) would be 100.

Comparative Example 5

A titanium oxide particle-metal particle dispersion liquid (C-5) for use in comparative evaluation was obtained by mixing the surface-protected metal particle dispersion liquid (3A) into the surface-modified titanium oxide particle dispersion liquid (2G) so that a mass ratio of the particles contained in each dispersion liquid (surface-modified titanium oxide particles/surface-protected metal particles) would be 100.

Comparative Example 6

A titanium oxide particle-metal particle dispersion liquid (C-6) for use in comparative evaluation was obtained by mixing the surface-protected metal particle dispersion liquid (3A) into the surface-modified titanium oxide particle dispersion liquid (2H) so that a mass ratio of the particles contained in each dispersion liquid (surface-modified titanium oxide particles/surface-protected metal particles) would be 100.

Comparative Example 7

A titanium oxide particle-metal particle dispersion liquid (C-7) for use in comparative evaluation was obtained by mixing the surface-protected metal particle dispersion liquid (3A) into the surface-modified titanium oxide particle dispersion liquid (2I) so that a mass ratio of the particles contained in each dispersion liquid (surface-modified titanium oxide particles/surface-protected metal particles) would be 100.

Comparative Example 8

A titanium oxide particle-metal particle dispersion liquid (C-8) for use in comparative evaluation was obtained by mixing the surface-protected metal particle dispersion liquid (3A) into the surface-modified titanium oxide particle dispersion liquid (2J) so that a mass ratio of the particles contained in each dispersion liquid (surface-modified titanium oxide particles/surface-protected metal particles) would be 100.

Comparative Example 9

A titanium oxide particle-metal particle dispersion liquid (C-9) for use in comparative evaluation was obtained by mixing the surface-protected metal particle dispersion liquid (3A) into the surface-modified titanium oxide particle dispersion liquid (2K) so that a mass ratio of the particles contained in each dispersion liquid (surface-modified titanium oxide particles/surface-protected metal particles) would be 100.

Comparative Example 10

A titanium oxide particle-metal particle dispersion liquid (C-10) for use in comparative evaluation was obtained by mixing the surface-protected metal particle dispersion liquid (3A) into the surface-modified titanium oxide particle dispersion liquid (2L) so that a mass ratio of the particles contained in each dispersion liquid (surface-modified titanium oxide particles/surface-protected metal particles) would be 100. The liquid obtained exhibited white turbidity, and precipitation was partially observed therein.

Comparative Example 11

A titanium oxide particle-metal particle dispersion liquid (C-11) for use in comparative evaluation was obtained by mixing a 1% by mass silver nitrate aqueous solution into the surface-modified titanium oxide particle dispersion liquid (2A) so that a mass ratio to the surface-modified titanium oxide particles (surface-modified titanium oxide particles/silver) would be 100. The liquid obtained exhibited white turbidity, and precipitation was partially observed therein.

Comparative Example 12

A binder-containing titanium oxide particle-metal particle dispersion liquid (C-12) was obtained in a similar manner as the working example 8, except that the titanium oxide particle-metal particle dispersion liquid (C-3) was used.

TABLE 4

| Working example/ Comparative example | Titanium oxide particle-metal particle dispersion liquid | Surface-modified titanium oxide particle dispersion liquid | Metal particle dispersion liquid | Mass ratio Surface-modified titanium oxide particles/Metal particles with protective agent adsorbed onto surfaces thereof | Dispersion particle diameter nm $D_{50}$ | $D_{90}$ |
|---|---|---|---|---|---|---|
| Working example 1 | E-1 | 2A | 3A | 100 | 15 | 26 |
| Working example 2 | E-2 | 2B | 3B | 400 | 13 | 24 |
| Working example 3 | E.3 | 2C | 3C | 200 | 24 | 46 |
| Working example 4 | E-4 | 2D | 3A | 100 | 16 | 30 |
| Working exampie 5 | E-5 | 2E | 3A | 100 | 18 | 39 |
| Working exampis 6 | E-6 | 2A | 3D | 100 | 32 | 85 |
| Working example 7 | E-7 | 2A | 3E | 1000 | 36 | 102 |
| Comparative example 1 | C-1 | 2A | — | — | 12 | 21 |
| Comparative example 2 | C-2 | — | 3A | — | 43 | 53 |
| Comparative example 3 | C-3 | 1A | 3A | 100 | 12 | 18 |
| Comparative example 4 | C-4 | 2F | 3A | 100 | 18 | 38 |
| Comparative example 5 | C-5 | 2G | 3A | 100 | 32 | 47 |
| Comparative example 6 | C-6 | 2H | 3A | 100 | 34 | 73 |
| Comparative example 7 | C-7 | 2I | 3A | 100 | 33 | 60 |
| Comparative example 8 | C-8 | 2J | 3A | 100 | 26 | 46 |
| Comparative example 9 | C-9 | 2K | 3A | 100 | 15 | 25 |
| Comparative example 10 | C-10 | 2L | 3A | 100 | 68 | 160 |
| Comparative example 11 | C-11 | 2A | Sliver aqueous solution | 100 | 78 | 265 |

TABLE 5

| Working example/ Comparative example | Titanium oxide particle-metal particle disper-sion liquid | Mass ratio Titanium oxide particles and metal particles/Binder |
|---|---|---|
| Working example 8 | E - 1 | 1.5 |
| Comparative example 12 | C - 3 | 1.5 |

Table 6 collectively shows the results of an antimicrobial property test and acetaldehyde gas decomposition capability test that were carried out as above in the working and comparative examples: as well as the presence or non-presence of precipitates (indicated as ○ if not present (favorable), indicated as x if present (unfavorable)).

TABLE 6

| Working example/ Comparative example | Binder | Antimicrobial property test: Antimicrobial activity value (dark place) *E. coli* | *Staphylococcus aureus* | Antimicrobial activity value (under visible light irradiation) *E. coli* | *Staphylococcus aureus* | Evaluation | Acetaldehyde gas decomposition test (under LED irradiation) Time | Evaluation | Presence or non-presence of precipitates |
|---|---|---|---|---|---|---|---|---|---|
| Working example 1 | Not used | 4.8 | 4.5 | 5.1 | 4.9 | ◎ | 3.0 | ◎ | ○ |
| Working example 2 | Not used | 4.2 | 4.0 | 4.6 | 4.4 | ◎ | 3.8 | ◎ | ○ |
| Working example 3 | Not used | 4.6 | 4.3 | 4.9 | 4.7 | ◎ | 3.8 | ◎ | ○ |
| Working example 4 | Not used | 4.8 | 4.5 | 5.1 | 4.8 | ◎ | 2.5 | ◎ | ○ |
| Working example 5 | Not used | 4.8 | 4.5 | 5.2 | 4.8 | ◎ | 3.2 | ◎ | ○ |
| Working example 6 | Not used | 3.5 | 3.1 | 3.8 | 3.4 | ○ | 5.4 | ○ | ○ |
| Working example 7 | Not used | 2.5 | 2.3 | 2.9 | 2.7 | ○ | 7.2 | ○ | ○ |
| Comparative example 1 | Not used | 0.2 | 0.1 | 4.5 | 4.2 | X | 2.8 | ◎ | ○ |
| Comparative example 2 | Not used | 4.6 | 4.4 | 4.8 | 4.4 | ◎ | Did not decompose | X | ○ |
| Comparative example 3 | Not used | 4.8 | 4.6 | 4.8 | 4.6 | ◎ | 20 hours or more | X | ○ |
| Comparative example 4 | Not used | 4.6 | 4.4 | 4.7 | 4.4 | ◎ | Did not decompose | X | ○ |
| Comparative example 5 | Not used | 4.7 | 4.4 | 4.8 | 4.5 | ◎ | Did not decompose | X | ○ |
| Comparative example 6 | Not used | 4.5 | 4.3 | 4.5 | 4.4 | ◎ | Did not decompose | X | ○ |
| Comparative example 7 | Not used | 4.8 | 4.4 | 4.8 | 4.5 | ◎ | Did not decompose | X | ○ |
| Comparative example 8 | Not Used | 4.8 | 4.8 | 4.8 | 4.5 | ◎ | Did not decompose | X | ○ |
| Comparative example 9 | Not used | 4.6 | 4.4 | 4.5 | 4.5 | ◎ | 20 hours or more | X | ○ |
| Comparative example 10 | Not used | 4.7 | 4.4 | 4.0 | 3.8 | ○ | 5.8 | O | X |
| Comparative example 11 | Not used | 4.8 | 4.6 | 4.5 | 4.2 | ◎ | 10.2 | Δ | X |
| Working example 8 | Used | 4.6 | 4.3 | 4.8 | 4.5 | ◎ | 9.8 | ○ | ○ |
| Comparative example 12 | Used | 4.6 | 4.3 | 4.5 | 4.2 | ◎ | Did not decompose | X | ○ |

The working example 1 and comparative example 1 indicate that an antimicrobial property in a dark place was unable to be achieved with the titanium oxide particles alone.

The working example 1 and comparative example 2 indicate that a photocatalytic activity under visible light irradiation cannot be achieved with the metal particles alone.

The working example 1 and comparative examples 3 and 9; as well as the working example 8 and comparative example 12 indicate that a low photocatalytic activity under visible light irradiation was observed when the titanium oxide surface was not modified by the iron (Fe) component and the silicon (Si) component.

The working example 1 and comparative example 10 indicate that the components agglutinated and precipitated when the titanium oxide surface was modified by the iron (Fe) component alone.

The working example 1 and comparative example 11 indicate that a lower photocatalytic activity under visible light irradiation was observed, and the components agglutinated and precipitated, when the surface-modified titanium oxide surface was further modified by the silver component.

The working examples 1 to 7 and comparative examples 4 to 8 indicate that a photocatalytic activity under visible light irradiation was unable to be achieved when the tin component and transition metal component were not solid-dissolved in titanium oxide.

The invention claimed is:

1. A titanium oxide particle-metal particle composition comprising two kinds of particles which are:

(i) titanium oxide particles with a tin component and a visible light activity-enhancing transition metal component being solid-dissolved therein, and with the surfaces of the titanium oxide particles being modified by an iron component and a silicon component that are not solid-dissolved in the titanium oxide particles; and (ii) antimicrobial metal-containing metal particles;

wherein a mass ratio of the iron component (in terms of oxide) modifying the surfaces of the titanium oxide particles (i) to titanium oxide ($TiO_2/Fe_2O_3$) is 10 to 100,000, and a mass ratio of the silicon component (in terms of oxide) modifying the surfaces of the titanium oxide particles (i) to titanium oxide ($TiO_2/SiO_2$) is 1 to 10,000;

wherein the titanium oxide particles in the titanium oxide particle dispersion liquid have a particle diameter of 3 to 50 nm, the particle diameter being a 50% cumulative distribution diameter (D50) on volumetric basis that is measured by a dynamic light scattering method using a laser light; and wherein the visible light activity-enhancing transition metal component solid-dissolved in the titanium oxide particles (i) is at least one kind selected from molybdenum, tungsten and vanadium.

2. The titanium oxide particle-metal particle composition according to claim 1, wherein a protective agent is adsorbed onto the surfaces of the antimicrobial metal-containing metal particles (ii).

3. The titanium oxide particle-metal particle composition according to claim 1, wherein an antimicrobial metal contained in the antimicrobial metal-containing metal particles (ii) is at least one kind of metal selected from silver, copper and zinc.

4. The titanium oxide particle-metal particle composition according to claim 3, wherein the antimicrobial metal contained in the antimicrobial metal-containing metal particles (ii) at least contains silver.

5. The titanium oxide particle-metal particle composition according to claim 1, wherein the tin component is contained and solid-dissolved in the titanium oxide particles (i) by an amount of 1 to 1,000 in terms of a molar ratio to titanium oxide ($TiO_2/Sn$).

6. The titanium oxide particle-metal particle composition according to claim 1, wherein the mass ratio of the iron component (in terms of oxide) modifying the surfaces of the titanium oxide particles (i) to titanium oxide ($TiO_2/Fe_2O_3$) is 20 to 100,000, and the mass ratio of the silicon component (in terms of oxide) modifying the surfaces of the titanium oxide particles (i) to titanium oxide ($TiO_2/SiO_2$) is 2 to 10,000.

7. The titanium oxide particle-metal particle composition according to claim 1, wherein the visible light activity-enhancing transition metal component solid-dissolved in the titanium oxide particles (i) is at least one kind selected from molybdenum and tungsten.

8. The titanium oxide particle-metal particle composition according to claim 1, wherein the molybdenum, tungsten and vanadium components are each solid-dissolved in the titanium oxide particles (i) by an amount of 1 to 10,000 in terms of a molar ratio to titanium oxide ($TiO_2/Mo$, $TiO_2/W$ or $TiO_2/V$).

9. The titanium oxide particle-metal particle composition according to claim 1, wherein a mass ratio between the titanium oxide particles (i) and an antimicrobial metal component (M) contained in the metal particles (ii) ($TiO_2/M$) is 1 to 100,000.

10. The titanium oxide particle-metal particle composition according to claim 1, wherein the composition further comprises a binder.

11. The titanium oxide particle-metal particle composition according to claim 10, wherein the binder is a silicon compound-based binder.

12. The titanium oxide particle-metal particle composition according to claim 1, wherein the composition is a titanium oxide particle-metal particle dispersion liquid.

13. The titanium oxide particle-metal particle composition according to claim 1, wherein the composition is a titanium oxide particle-metal particle thin film.

14. A member having the composition according to claim 13 on a surface thereof.

15. A method for producing the composition according to claim 12, comprising:

(1) a step of producing a tin component and transition metal component-containing peroxotitanic acid solution from a raw material titanium compound, tin compound, transition metal compound, basic substance, hydrogen peroxide and aqueous dispersion medium;

(2) a step of obtaining a dispersion liquid of titanium oxide particles with the tin and transition metal components being solid-dissolved therein, by heating the tin component and transition metal component-containing peroxotitanic acid solution produced in the step (1) at 80 to 250° C. under a controlled pressure;

(3) a step of producing a solution or dispersion liquid of an iron component and a silicon component from an iron compound, silicon compound and aqueous dispersion medium;

(4) a step of obtaining a dispersion liquid of titanium oxide particles surface-modified by the iron and silicon components, by mixing the titanium oxide particle dispersion liquid produced in the step (2) and the solution or dispersion liquid of the iron and silicon components that has been produced in the step (3);

(5) a step of respectively producing a solution containing a raw material antimicrobial metal compound, and a solution containing a reductant for reducing the raw material antimicrobial metal compound and a protective agent for coating and protecting metal particles;

(6) a step of producing a metal particle dispersion liquid by mixing the solutions obtained in the step (5) which are the solution containing the raw material antimicrobial metal compound, and the solution containing the reductant for reducing the raw material antimicrobial metal compound and the protective agent for coating and protecting metal particles;

(7) a step of washing the metal particle dispersion liquid produced in the step (6) by a membrane filtration method, using an aqueous dispersion medium; and (8) a step of mixing the titanium oxide particle dispersion liquid obtained in the step (4) and the metal particle dispersion liquid obtained in the step (7).

* * * * *